United States Patent
Ogihara et al.

(10) Patent No.: US 11,633,513 B2
(45) Date of Patent: *Apr. 25, 2023

(54) ULTRAVIOLET RAY IRRADIATION DEVICE AND ULTRAVIOLET RAY BLOCKING UNIT

(71) Applicant: Work Solution Co., Ltd., Nagano (JP)

(72) Inventors: Shinji Ogihara, Nagano (JP); Kiyomi Shimada, Nagano (JP); Haruhiko Miyamoto, Nagano (JP)

(73) Assignee: WORK SOLUTION CO., LTD., Nagano (JP)

(*) Notice: Subject to any disclaimer, the term of this patent is extended or adjusted under 35 U.S.C. 154(b) by 239 days.

This patent is subject to a terminal disclaimer.

(21) Appl. No.: 16/953,335

(22) Filed: Nov. 20, 2020

(65) Prior Publication Data
US 2021/0353807 A1    Nov. 18, 2021

(30) Foreign Application Priority Data
May 18, 2020    (JP) .............................. JP2020-086488

(51) Int. Cl.
*A61L 2/26*    (2006.01)
*A61L 2/10*    (2006.01)

(52) U.S. Cl.
CPC .................. *A61L 2/26* (2013.01); *A61L 2/10* (2013.01); *A61L 2202/11* (2013.01); *A61L 2202/121* (2013.01); *A61L 2202/122* (2013.01)

(58) Field of Classification Search
CPC ........ A61L 2/26; A61L 2/10; A61L 2202/121; A61L 2201/122

USPC ........................... 250/453.11, 454.11, 455.11
See application file for complete search history.

(56) References Cited

U.S. PATENT DOCUMENTS

2021/0177999 A1*   6/2021   Ogihara ................ G01J 5/0025

FOREIGN PATENT DOCUMENTS

JP             201763900 A        4/2017

OTHER PUBLICATIONS

International Search Report in PCT/JP2021/018685, dated Aug. 3, 2021. 4pp.

* cited by examiner

*Primary Examiner* — Nicole M Ippolito
(74) *Attorney, Agent, or Firm* — Hauptman Ham, LLP

(57) ABSTRACT

To provide an ultraviolet ray irradiation device which, when an operator inserts a glove to the device, prevents irradiation of ultraviolet rays to the outside thus further enhancing safety. An ultraviolet ray irradiation device includes: a sterilization chamber housing having an insertion opening through which a hand on which a glove is mounted is inserted into a sterilization chamber; an ultraviolet ray irradiating unit which irradiates ultraviolet rays to the chamber; ultraviolet ray blocking elastic bodies disposed so as to traverse an insertion direction of the hand, and allowing the hand to penetrate the elastic bodies; and a frame body supporting peripheral edge portions of the stacked elastic bodies. A plurality of cuts are radially formed in the elastic bodies. A plurality of elastic members are formed between the cuts. The respective elastic bodies are mounted on the frame body such that the cuts are displaced from each other.

11 Claims, 12 Drawing Sheets

ULTRAVIOLET RAY IRRADIATION DEVICE AND ULTRAVIOLET RAY BLOCKING UNIT

RELATED APPLICATIONS

The present application claims priority to Japanese Application Number 2020-086488, filed May 18, 2020, the disclosure of which is hereby incorporated by reference herein in its entirety.

BACKGROUND OF THE INVENTION

Field of the Invention

The present invention relates to an ultraviolet ray irradiation device and an ultraviolet ray blocking unit.

Description of the Related Art

Sterilization by ultraviolet rays exhibits a highly favorable effect against virus or bacteria in a wide range including norovirus, salmonella and O157. Accordingly, in various fields including food industry and medical field, an ultraviolet ray irradiation device which uses ultraviolet rays has been attracting attentions.

Although ultraviolet rays exhibit a highly favorable effect against virus or bacteria in a wide range, on the other hand, there has been also reported that, when ultraviolet rays are irradiated to an operator or other operators around him, the ultraviolet rays adversely affect the operator or other operators around him. Accordingly, it is important for an ultraviolet ray irradiation device to ensure high safety such that ultraviolet rays irradiated in a sterilization chamber formed in a sterilization chamber housing do not adversely affect an operator or other operators around him. Therefore, an ultraviolet ray irradiation device which exhibits high safety has been proposed by taking into account the above problem (see JP 2017-63900 A, for example).

FIG. 15 is a perspective view for describing an ultraviolet ray irradiation device 900 described in JP 2017-63900 A. The ultraviolet ray irradiation device 900 described in JP 2017-63900 A includes, as shown in FIG. 15, a sterilization chamber housing 920 having an insertion opening 910 through which a hand on which a glove G is mounted is inserted; ultraviolet ray irradiation lamps 930 which irradiate ultraviolet rays to a sterilization chamber 921 formed in the sterilization chamber housing 920; a guide portion 940 having a sleeve shape extending from an edge portion of the insertion opening 910 in a direction toward an inside of the sterilization chamber 921, guiding an insertion of the hand on which the glove is mounted and blocking the ultraviolet rays; and an ultraviolet ray blocking plate 950 which covers a front surface and side surfaces of the insertion opening 910.

The ultraviolet ray irradiation device 900 described in JP 2017-63900 A is an ultraviolet ray irradiation device of a type where the hand on which the glove G is mounted is inserted in a downward direction from above. On the other hand, with respect to the ultraviolet ray irradiation device 900, an ultraviolet ray irradiation device of a type where the hand on which the glove G is mounted is inserted in an upward direction from below is also described.

The ultraviolet ray irradiation device 900 described in JP 2017-63900 A is an ultraviolet ray irradiation device which sterilizes a surface of the glove G by irradiating ultraviolet rays to the glove G which is mounted on a hand of an operator. In other words, when the hand of the operator on which the glove G is mounted is inserted into the sterilization chamber 921 through the insertion opening 910, the ultraviolet ray irradiation lamps 930 are turned on in the sterilization chamber 921 so that ultraviolet rays are irradiated to the surface of the glove G. With such a configuration, the surface of the glove G can be sterilized.

Further, the ultraviolet ray irradiation device 900 described in JP 2017-63900 A includes, as described above, the guide portion 940 having a sleeve shape and the ultraviolet ray blocking plate 950. Accordingly, it is possible to prevent the occurrence of a state where ultraviolet rays which are irradiated to the sterilization chamber 921 are irradiated to an operator who is receiving sterilization at the moment and other operators around the operator. As a result, the ultraviolet ray irradiation device 900 described in JP 2017-63900 A may be an ultraviolet ray irradiation device which ensures high safety where the ultraviolet rays irradiated in the sterilization chamber 921 do not adversely affect the operator who is receiving sterilization at the moment and other operators around the operator.

SUMMARY OF THE INVENTION

As described above, the ultraviolet ray irradiation device 900 described in JP 2017-63900 A is an ultraviolet ray irradiation device which exhibits high safety. However, there has been a demand for the development of an ultraviolet ray irradiation device having higher safety. Under such a circumstance, if ultraviolet rays can be blocked with certainty so that the ultraviolet rays do not leak out from an insertion opening, it is possible to prevent the occurrence of a state where ultraviolet rays are irradiated to an operator who is receiving sterilization at the moment and other operators around the operator. Accordingly, to realize an ultraviolet ray irradiation device which further enhances safety, it is necessary to prevent ultraviolet rays from being irradiated to the outside of a sterilization chamber with certainty when an operator inserts a glove into the ultraviolet ray irradiation device.

Particularly, depending on the content of an operation which an operator performs, there arises a case where the operator uses a short glove which cannot cover a portion ranging from a wrist to an elbow of the operator, and the operator also cannot wear an arm cover which covers the wrist and the elbow portion. In such a case, a hand on which a glove G is mounted is inserted into the sterilization chamber 921 through the insertion opening 910 in a state where the wrist and the elbow of the operator are exposed, that is, in a state where the wrist and the elbow are in a bare skin state. In this case, the wrist and the elbow of the operator are positioned outside of the insertion opening. However, when ultraviolet rays are leaked to the outside from the ultraviolet ray irradiation device, there arises a possibility that the leaked ultraviolet rays are irradiated also to the wrist and the elbow. To cope with also such a case, it is important to prevent with certainty the irradiation of ultraviolet rays to the outside of the ultraviolet ray irradiation device.

The present invention has been made in view of the above-mentioned circumstances, and it is an object of the present invention to provide an ultraviolet ray irradiation device which sterilizes a surface of a glove which is mounted on a hand of an operator and is made of an ultraviolet ray non-transmitting material by irradiating ultraviolet rays to the glove, wherein the ultraviolet ray irradiation device can further enhance safety by preventing with certainty the irradiation of the ultraviolet rays to the outside of the ultraviolet ray irradiation device when the glove of the operator is inserted into the ultraviolet ray irradiation device.

It is another object of the present invention to provide an ultraviolet ray blocking unit which can prevent with certainty the irradiation of ultraviolet rays to the outside of the ultraviolet ray irradiation device when a glove of an operator is inserted into the ultraviolet ray irradiation device and can facilitate a maintenance of the ultraviolet ray irradiation device.

[1] According to an aspect of the present invention, there is provide an ultraviolet ray irradiation device which sterilizes a surface of a glove which is mounted on a hand of an operator and is made of an ultraviolet ray non-transmitting material by irradiating ultraviolet rays to the glove, wherein the ultraviolet ray irradiation device includes: a sterilization chamber housing formed of an ultraviolet ray blocking member configured to block the ultraviolet rays, the sterilization chamber housing having a sterilization chamber therein, and having an insertion opening through which the hand on which the glove is mounted is insertable into the sterilization chamber; an ultraviolet ray irradiation unit disposed in the sterilization chamber housing and configured to irradiate the ultraviolet rays to the sterilization chamber; an ultraviolet ray blocking elastic body formed of a thin plate-like member having ultraviolet ray non-transmitting property and elasticity, disposed so as to traverse an insertion direction of the hand on which the glove G is mounted when the hand on which the glove G is mounted is inserted into the sterilization chamber through the insertion opening, and allowing the hand on which the glove G is mounted to penetrate the ultraviolet ray blocking elastic bodies; and a frame body disposed along a peripheral edge portion of the insertion opening, the frame body allowing the respective ultraviolet ray blocking elastic bodies to be mounted on the frame body by supporting peripheral edge portions of the respective ultraviolet ray blocking elastic bodies in a state where a plurality of the ultraviolet ray blocking elastic bodies are stacked, wherein the ultraviolet ray blocking elastic body is formed such that a plurality of cuts are formed in the ultraviolet ray blocking elastic body along a plurality of lines extending radially from a predetermined position on a plate surface of the ultraviolet ray blocking elastic body toward a peripheral edge portion of the ultraviolet ray blocking elastic body thus forming the plurality of elastic members between the cuts, wherein a distal end portion of each of the plurality of elastic members which is positioned on a side of the predetermined position forms a free end which is freely movable in a frontward and backward direction of the ultraviolet ray blocking elastic body, and the respective ultraviolet ray blocking elastic bodies mounted on the frame body are mounted on the frame body such that the plurality of cuts formed in at least one ultraviolet ray blocking elastic body among the respective ultraviolet ray blocking elastic bodies are displaced with respect to the plurality of cuts of other ultraviolet ray blocking elastic bodies along the plate surfaces.

[2] In the ultraviolet ray irradiation device according to the present invention, it is preferable that the respective ultraviolet ray blocking elastic bodies mounted on the frame body be formed of an ultraviolet ray blocking elastic body having the same number of cuts.

[3] In the ultraviolet ray irradiation device according to the present invention, it is preferable that among the respective ultraviolet ray blocking elastic bodies mounted on the frame body, the ultraviolet ray blocking elastic body in which the cuts, the number of which differs from the number of cuts in other ultraviolet ray blocking elastic bodies, exist.

[4] In the ultraviolet ray irradiation device according to the present invention, it is preferable that the respective ultraviolet ray blocking elastic bodies mounted on the frame body be formed of an ultraviolet ray blocking elastic body where a position at which respective distal end portions of the plurality of elastic members formed on the respective ultraviolet ray blocking elastic bodies merge exists at the same position in the respective ultraviolet ray blocking elastic bodies.

[5] In the ultraviolet ray irradiation device according to the present invention, it is preferable that in the respective ultraviolet ray blocking elastic bodies mounted on the frame body, positions at which respective distal end portions of the plurality of elastic members formed on the respective ultraviolet ray blocking elastic bodies merge exist at positions spaced apart from each other in a diameter direction with respect to the respective ultraviolet ray blocking elastic bodies.

[6] In the ultraviolet ray irradiation device according to the present invention, it is preferable that among the respective ultraviolet ray blocking elastic bodies mounted on the frame body, an unevenness exist on a plate surface of at least one ultraviolet ray blocking elastic body out of the ultraviolet ray blocking elastic bodies which face each other.

[7] In the ultraviolet ray irradiation device according to the present invention, it is preferable that the respective ultraviolet ray blocking elastic bodies mounted on the frame body be stacked in a state where the respective ultraviolet ray blocking elastic bodies are disposed close to each other or in a state where the respective ultraviolet ray blocking elastic bodies are brought into contact with each other.

[8] In the ultraviolet ray irradiation device according to the present invention, it is preferable that The ultraviolet ray irradiation device according to any one of claims 1 to 6, wherein the respective ultraviolet ray blocking elastic bodies mounted on the frame body be stacked in a state where the respective ultraviolet ray blocking elastic bodies are spaced apart from each other with a predetermined distance therebetween.

[9] In the ultraviolet ray irradiation device according to the present invention, it is preferable that at positions of the distal end portion of the plurality of elastic members, a space portion surrounded by the distal end portions be formed.

[10] In the ultraviolet ray irradiation device according to the present invention, it is preferable that the frame body have antibacterial property.

[11] According to another aspect of the present invention, there is provided an ultraviolet ray blocking unit which is detachably mounted on a sterilization chamber housing of an ultraviolet ray irradiation device which sterilizes a surface of a glove which is mounted on a hand of an operator and is made of an ultraviolet ray non-transmitting material by irradiating ultraviolet rays to the glove, the ultraviolet ray blocking unit preventing irradiation of the ultraviolet rays to the outside of the ultraviolet ray irradiation device when the operator inserts the glove into the ultraviolet ray irradiation device, wherein the ultraviolet ray irradiation device includes: a sterilization chamber housing formed of an ultraviolet ray blocking member configured to block the ultraviolet rays, the sterilization chamber housing having a sterilization chamber in the sterilization chamber housing, and having an insertion opening through which the hand on which the glove is mounted is insertable into the sterilization chamber; an ultraviolet ray irradiation unit disposed in the sterilization chamber housing and configured to irradiate the ultraviolet rays to the sterilization chamber, the ultraviolet ray blocking unit comprises: an ultraviolet ray blocking elastic body formed of a thin plate-like member having ultraviolet ray non-transmitting property and elasticity, disposed so as to traverse an insertion direction of the hand when the hand on which the glove G is mounted is inserted into the sterilization chamber through the insertion opening, and allowing the hand on which the glove G is mounted to penetrate the ultraviolet ray blocking elastic bodies; and a frame body disposed along a peripheral edge portion of the insertion opening, the frame body allowing the respective ultraviolet ray blocking elastic bodies to be mounted on the frame body by supporting peripheral edge portions of the respective ultraviolet ray blocking elastic bodies in a state where a plurality of the ultraviolet ray blocking elastic bodies are stacked, and the ultraviolet ray blocking elastic body is formed such that a plurality of cuts are formed in the ultraviolet ray blocking elastic body along a plurality of lines extending radially from a predetermined position on a plate surface of the ultraviolet ray blocking elastic body toward a peripheral edge portion of the ultraviolet ray blocking elastic body thus forming the plurality of elastic members between the cuts, wherein a distal end portion of each of the plurality of elastic members which is positioned on a side of the predetermined position forms a free end which is freely movable in a frontward and backward direction of the ultraviolet ray blocking elastic body, and the respective ultraviolet ray blocking elastic bodies mounted on the frame body are mounted on the frame body such that the plurality of cuts formed in at least one ultraviolet ray blocking elastic body among the respective ultraviolet ray blocking elastic bodies are displaced with respect to the plurality of cuts of other ultraviolet ray blocking elastic bodies along the plate surfaces.

According to the ultraviolet ray irradiation device of the present invention, in the ultraviolet ray irradiation device which sterilizes a surface of a glove which is mounted on a hand of an operator and is made of an ultraviolet ray non-transmitting material by irradiating ultraviolet rays to the glove, it is possible to provide the ultraviolet ray irradiation device which can further enhance safety by preventing with certainty the irradiation of the ultraviolet rays to the outside of the ultraviolet ray irradiation device when the glove of the operator is inserted into the ultraviolet ray irradiation device.

According to the ultraviolet ray blocking unit of the present invention, it is possible to provide the ultraviolet ray blocking unit which can prevent with certainty the irradiation of ultraviolet rays to the outside of an ultraviolet ray irradiation device when a glove of an operator is inserted into the ultraviolet ray irradiation device and can facilitate a maintenance of the ultraviolet ray irradiation device.

Also in the ultraviolet ray blocking unit according to the present invention, it is preferable that the ultraviolet ray blocking unit have the respective technical features described in [2] to [10] which the ultraviolet ray irradiation device according to the present invention has.

DETAILED DESCRIPTION OF THE PREFERRED EMBODIMENTS

Figure 1:
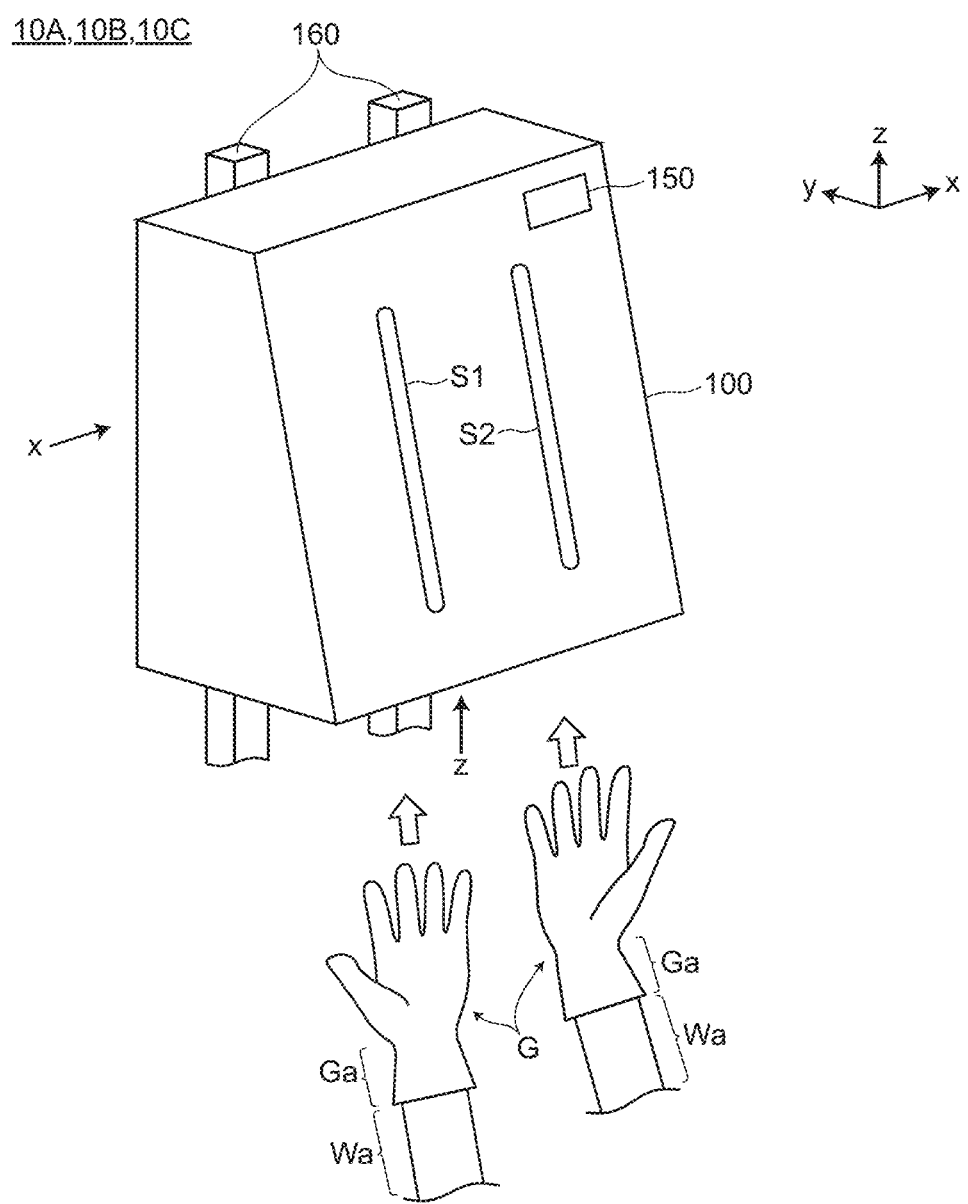
FIG. 1 is a constitutional view of an external appearance of an ultraviolet ray irradiation device according to an embodiment.

Hereinafter, an ultraviolet ray irradiation device according to the present invention and an ultraviolet ray blocking unit according to the present invention are described based on respective embodiments described below. The structures and the like shown in respective drawings which describe the respective embodiments are schematic views and hence, the indication of sizes and angles does not always reflect actual sizes and angles.

Embodiment 1

First, the configuration of an ultraviolet ray irradiation device 10A according to an embodiment 1 is described with reference to FIG. 1 to FIG. 7. As shown in FIG. 1 to FIG. 7, the ultraviolet ray irradiation device 10A according to the embodiment 1 includes: a sterilization chamber housing 100 which has a sterilization chamber 110 therein and insertion openings 120 through each of which a hand on which the glove G is mounted is inserted into the sterilization chamber 110; an ultraviolet ray irradiation unit 130 which is disposed in the sterilization chamber housing 100 and irradiates ultraviolet rays to the sterilization chamber 110; a display unit 150 disposed on a front surface of the sterilization chamber housing 100; support struts 160 which elevatably support the sterilization chamber housing 100 along a z axis; and ultraviolet ray blocking elastic bodies 210, 220 which are disposed so as to traverse an insertion direction of the hand on which the glove G is mounted when the hand is inserted into the sterilization chamber 110 through the insertion opening 120, and respectively have cuts C which allow the penetration of the hand on which the glove G is mounted; and a frame body 230 which is disposed along a peripheral edge portion 120a of the insertion opening 120 and is fixed to peripheral edge portions 210a, 220a of the ultraviolet ray blocking elastic bodies 210, 220.

The ultraviolet ray irradiation unit 130 is formed of a plurality of ultraviolet ray irradiation lamps. Accordingly, in the description made hereinafter, there is also a case where "ultraviolet ray irradiation unit 130" is expressed as "a plurality of ultraviolet ray irradiation lamps 130" or simply expressed as "ultraviolet ray irradiation lamp 130". The ultraviolet ray blocking elastic bodies 210, 220 and the frame body 230 are described in detail later.

The ultraviolet ray irradiation device 10A according to the embodiment 1 includes bare skin detection units 310 each of which forms an insertion depth detection unit which detects that the hand on which the glove G is mounted is inserted into the sterilization chamber 110 by a predetermined depth. As the bare skin detection unit 310, for example, an infrared sensor can be used. The infrared sensor used in the ultraviolet ray irradiation device 10A according to the embodiment 1 is a sensor which detects an infrared ray of a wavelength emitted from an object having a temperature substantially equal to a bare skin temperature of a human out of infrared rays received in a state where the hand on which the glove G is mounted is inserted through the insertion opening 120. Accordingly, the bare skin detection unit 310 can detect the exposed bare skin. The detail of the bare skin detection unit 310 is described later.

The ultraviolet ray irradiation device 10A according to the embodiment 1 is a type where a hand on which the glove G is mounted is inserted into the sterilization chamber 110 in an upward direction from below (see FIG. 1). Accordingly, the insertion opening 120 is formed in a lower surface side of the sterilization chamber housing 100 (see FIG. 2). Two insertion openings 120 are formed corresponding to left and right hands. To describe these two insertion openings 120 collectively, the expression "a pair of insertion openings 120" may be also adopted. In inserting the hand on which the glove G is mounted in the sterilization chamber 110, the hand is inserted into the sterilization chamber 110 in a state where palms of left and right hands of the operator W are respectively directed toward a side of a face of the operator W.

The glove G is a glove which is made of an ultraviolet ray non-transmitting material. For example, the glove G is formed using a lubber material such as nitrile or latex or thermoplastic resin which contains an ultraviolet ray blocking material such as titanium oxide. The glove G is of a short length which covers a range from fingertips to a wrist of an operator. Accordingly, in a case where an operator W wears an operation-use clothing having short sleeves, when the glove G is mounted on the hand of the operator W, although the hand of the operator W is covered by the glove G including the wrist of the operator W, a region Wa of an arm of the operator W which is not covered by the glove G is brought into a state where his/her skin is exposed.

In the glove G, assume a portion of the glove G which covers the wrist of the operator W as "a wrist portion Ga of the glove G". The region Wa of the arm of the operator W which is not covered by the glove G is referred to as "a bare skin region Wa right below the wrist portion Ga of the glove G" or simply "the bare skin region Wa".

Hereinafter, the main constitutional elements of the ultraviolet ray irradiation device 10A according to the embodiment 1 are described in detail in order. First, the sterilization chamber housing 100 is described with reference to FIG. 1 and FIG. 2.

The sterilization chamber housing 100 is formed of an ultraviolet ray blocking member which blocks ultraviolet rays such as a metal plate. Two slits S1, S2 are formed at predetermined interval on a front surface of the sterilization chamber housing 100 (a surface on a side facing a face of the operator W) (see FIG. 1). A semi-transparent acrylic plate or the like to which processing which can block ultraviolet rays such as smoke processing is applied is fitted in these two slits S1, S2.

With such a configuration, when the operator W inserts hands on which gloves G are mounted into the sterilization chamber 110, it is possible to visually check whether or not the hands on which the gloves G are mounted are inserted into the sterilization chamber 110 by a predetermined depth without being affected by ultraviolet rays. In this embodiment, "a state where the hand is inserted into the sterilization chamber 110 by a predetermined depth" means "a state where the hand is inserted into the sterilization chamber 110 by a depth which enables appropriate sterilization".

The sterilization chamber housing 100 includes a sterilization chamber housing member 170 which forms one surface of the sterilization chamber housing 100, and the above-mentioned insertion openings 120 are formed in the sterilization chamber housing member 170. In the ultraviolet ray irradiation device 10A according to the embodiment 1, the insertion openings 120 are formed on a lower surface side of the sterilization chamber housing 100 and hence, the sterilization chamber housing member 170 forms a portion of a bottom surface of the sterilization chamber housing 100. The bare skin detection unit 310 is disposed in the sterilization chamber housing member 170.

A plurality of ultraviolet ray irradiation lamps 130 disposed in the sterilization chamber housing 100 are mercury-arc lamps which emit ultraviolet rays having a wavelength of 185 nm to 280 nm. The plurality of ultraviolet ray irradiation lamps 130 are disposed on an inner wall surface 110a of an upper surface side of the sterilization chamber 110 parallel to each other. The respective ultraviolet ray irradiation lamps 130 are disposed parallel to each other at predetermined interval. In the sterilization chamber 110, the plurality of ultraviolet ray irradiation lamps 130 extend over the substantially whole region in a width direction (x axis direction). A protective sheet 131 made of an ultraviolet ray transmitting material is disposed so as to cover the entirety of the plurality of ultraviolet ray irradiation lamps 130.

The protective sheet 131 is provided for preventing scattering of broken pieces of the ultraviolet ray irradiation lamp 130 in the sterilization chamber 110 even when the ultraviolet ray irradiation lamp 130 is broken. Although not shown in the drawings, a protective net may be disposed on a front side of the protective sheet 131. Also, not shown in the drawings, an aluminum foil to which wrinkling is applied and which forms a reflector adheres to respective inner wall surfaces of the sterilization chamber housing 100. The aluminum foil reflects and scatters ultraviolet rays irradiated in a direction from the ultraviolet ray irradiation lamp 130 toward the respective inner wall surfaces of the sterilization chamber 110.

Next, the ultraviolet ray blocking elastic bodies 210, 220 and the frame body 230 are described in detail with reference to FIG. 3A to FIG. 5.

Figure 3A:
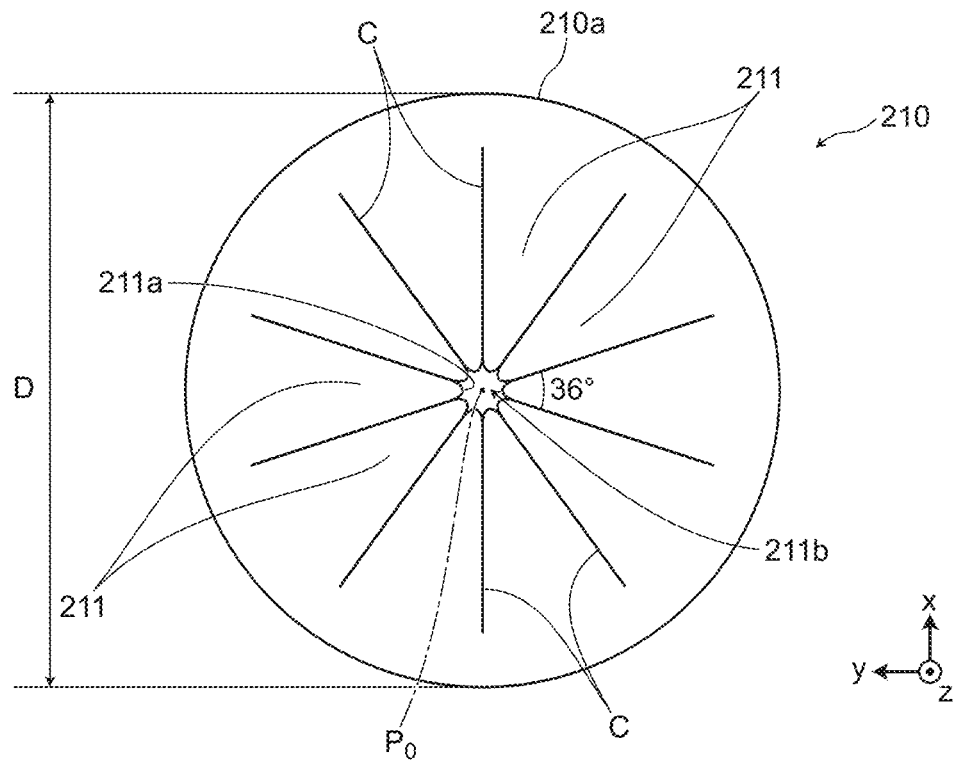
FIG. 3A and FIG. 3B are views for describing ultraviolet ray blocking elastic bodies 210, 220 used in the ultraviolet ray irradiation device 10A according to the embodiment 1.
Figure 3B:
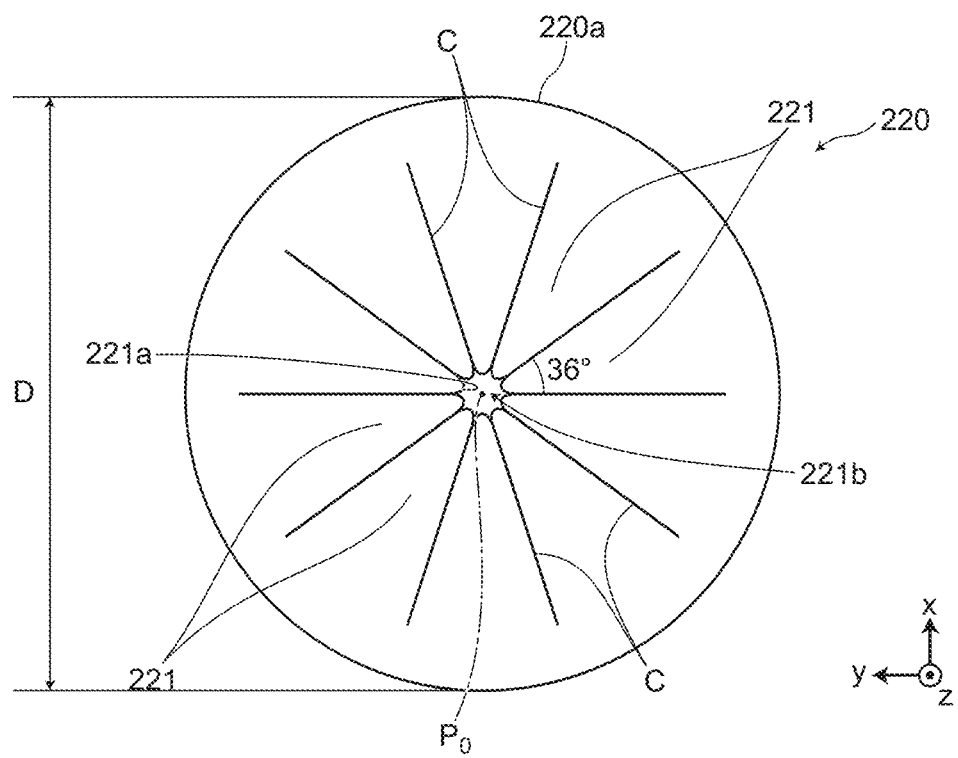

FIG. 3A and FIG. 3B are views for describing the ultraviolet the ray blocking elastic bodies 210, 220 used in the ultraviolet ray irradiation device 10A according to the embodiment 1. FIG. 3A is a plan view of the ultraviolet ray blocking elastic body 210, and FIG. 3B is a plan view of the ultraviolet ray blocking elastic body 220. In the description made hereinafter, there may be a case where the ultraviolet ray blocking elastic body 210 is referred to as a first ultraviolet ray blocking elastic body 210, and the ultraviolet ray blocking elastic body 220 is referred to as a second ultraviolet ray blocking elastic body 220. In a case where both the first ultraviolet ray blocking elastic body 210 and the second ultraviolet ray blocking elastic body 220 are indicated, the expression "ultraviolet ray blocking elastic bodies 210, 220" or "respective ultraviolet ray blocking elastic bodies 210, 220" may also be adopted.

In the ultraviolet ray irradiation device 10A according to the embodiment 1, assume that the first ultraviolet ray blocking elastic body 210 and the second ultraviolet ray blocking elastic body 220 are equal, and have the same shape and the same size. The ultraviolet ray blocking elastic bodies 210, 220 are respectively formed of a thin plate-like member having ultraviolet ray non-transmitting property and elasticity, and each of the ultraviolet ray blocking elastic bodies 210, 220 has a circular planar shape. The ultraviolet ray blocking elastic bodies 210, 220 can be formed using a synthetic rubber such as silicone rubber, natural rubber, or a synthetic resin. It is preferable that the first ultraviolet ray blocking elastic body 210 and the second ultraviolet ray blocking elastic body 220 have an antibacterial property on a plate surface by applying an antibacterial treatment to the plate surface. It is particularly preferable that the plate surface on a side where the plate surface is brought into contact with a hand on which the glove G is mounted have antibacterial property.

The ultraviolet ray blocking elastic bodies 210, 220 each have a diameter D of approximately 110 mm to 150 mm and a thickness t of approximately 0.5 mm to 3 mm. The plurality of cuts C are formed in the ultraviolet ray blocking elastic bodies 210, 220 such that the plurality of cuts C linearly and radially extend from a predetermined position on the plate surface of the ultraviolet ray blocking elastic body 210, 220 (assuming the center Po of the ultraviolet ray blocking elastic bodies 210, 220) toward a peripheral edge portion 210a, 220a of the ultraviolet ray blocking elastic body 210, 220. The cuts C do not reach the peripheral edge portions 210a, 220a of the respective ultraviolet ray blocking elastic bodies 210, 220.

In the ultraviolet ray irradiation device 10A according to the embodiment 1, the number of cuts C formed in each of the ultraviolet ray blocking elastic bodies 210, 220 is set to 10. These 10 cuts are formed by equally dividing 360 degrees by 10 so that an angle made by the cuts C disposed adjacently to each other becomes 36 degrees. Accordingly, in the first ultraviolet ray blocking elastic body 210, 10 pieces of elastic members 211 each having a "wedge shape" having a narrow distal end are formed, wherein each elastic member 211 is formed between the respective cuts C disposed adjacently to each other. Also in the second ultraviolet ray blocking elastic body 210, 10 pieces of elastic members 221 each having a "wedge shape" having a narrow distal end are formed, wherein each elastic member 221 is formed between the respective cuts C disposed adjacently to each other.

With respect to 10 pieces of elastic members 211 (also expressed as respective elastic members 211) of the first ultraviolet ray blocking elastic body 210, an end portion 211a (assuming as a distal end portion 211a) on a center Po side of the elastic member 211 forms a free end which is freely movable toward front and back directions of the first ultraviolet ray blocking elastic body 210. In the same manner, with respect to 10 pieces of elastic member 221 (also expressed as respective elastic members 221) of the second ultraviolet ray blocking elastic body 220, an end portion 221a (assuming as a distal end portion 221a) on the center Po side forms a free end which is freely removable toward front and back directions of the second ultraviolet ray blocking elastic body 220.

With respect to each elastic member 211 of the first ultraviolet ray blocking elastic body 210, a sharpened distal end portion is cut away so as to form a rounded distal end portion 211a. In this manner, with respect to each elastic member 211 of the first ultraviolet ray blocking elastic body 210, the sharpened distal end portion is cut away. Accordingly, at the respective distal end portions 211a of the respective elastic members 211 of the first ultraviolet ray blocking elastic bodies 210 (that is, the position where the respective distal end portions 211 marge), a space portion (penetration hole) 211b which is surrounded by the respective distal end portions 211a is formed.

Also with respect to the second ultraviolet ray blocking elastic body 220, a sharpened distal end portion is cut away so as to form a rounded distal end portion 221a. In this manner, with respect to each elastic member 221 of the ultraviolet ray blocking elastic body 220, the sharpened distal end portion is cut away. Accordingly, at the position where the respective distal end portions 221a of the respective elastic members 221 of the second ultraviolet ray blocking elastic bodies 220 marge, a space portion (penetration hole) 221b which is surrounded by the respective distal end portions 221a is formed.

The center of the space portion 211b surrounded by the respective distal end portions 211a of the respective elastic members 211 and the center of the space portion 221b surrounded by the respective distal end portions 221a of respective elastic members 221 are aligned with the center Po of the ultraviolet ray blocking elastic bodies 210, 220. The ultraviolet ray blocking elastic bodies 210, 220 having such a configuration are mounted on the frame body 230 in a stacked state (see FIG. 4A and FIG. 4B).

Figure 4A:
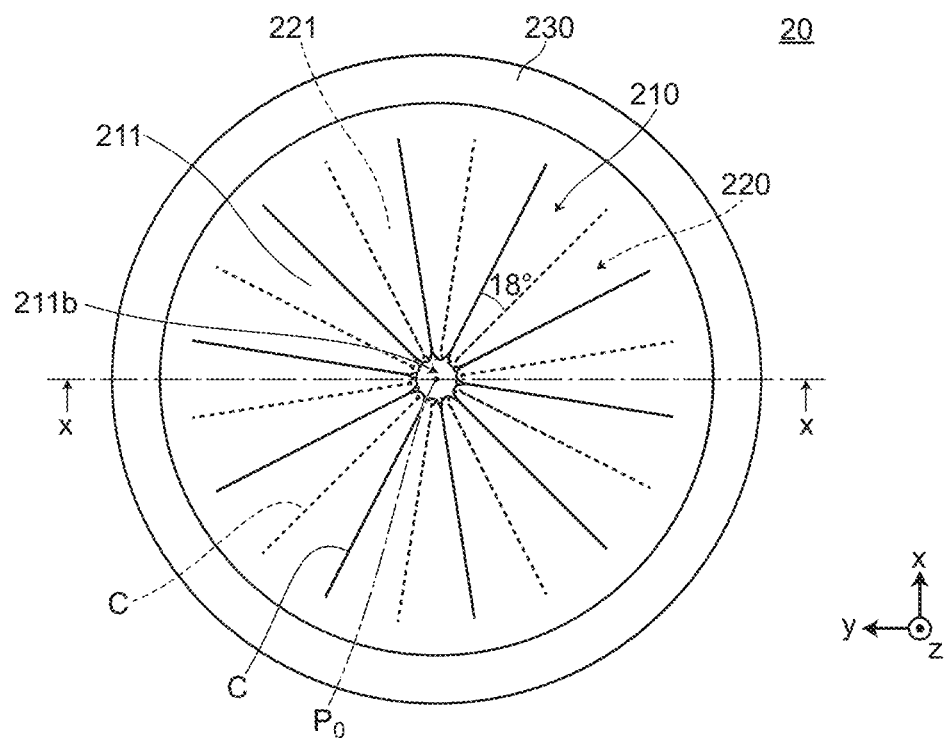
FIG. 4A and FIG. 4B are views showing an appearance where the ultraviolet ray blocking elastic bodies 210, 220 are mounted on a frame body 230 in a stacked state.
Figure 4B:
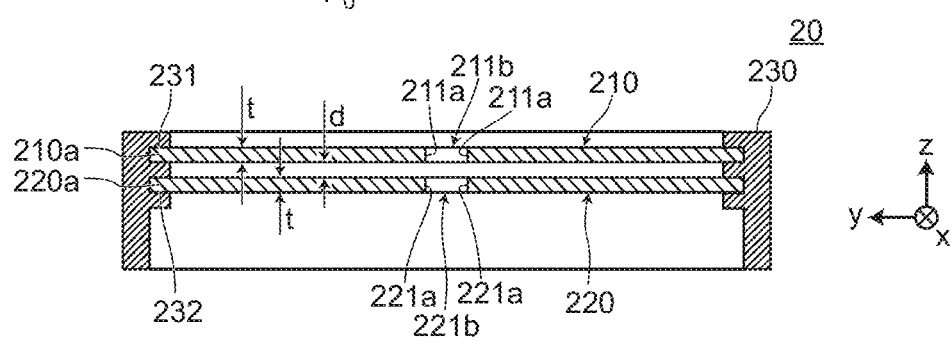

FIG. 4A and FIG. 4B are views showing an appearance where the ultraviolet ray blocking elastic bodies 210, 220 are mounted on a frame body 230 in a stacked state. FIG. 4A is a plan view of the appearance as viewed from a first ultraviolet ray blocking elastic body 210 side. FIG. 4B is a cross-sectional view taken along a line x-x in FIG. 4A as viewed in a direction x. The ultraviolet ray blocking unit 20 can be formed of: the ultraviolet ray blocking elastic bodies 210, 220; and the frame body 230.

As shown in FIG. 4A and FIG. 4B, peripheral edge portions 210a, 220a of the ultraviolet ray blocking elastic bodies 210, 220 are supported by receiving grooves 231, 232 formed in an inner peripheral surface of the frame body 230. With such a configuration, a state is brought about where the ultraviolet ray blocking elastic bodies 210, 220 are mounted on the frame body 230. It is preferable that the frame body 230 have antibacterial property. To realize such a state, it is preferable that an antibacterial treatment be applied to a surface of the frame body 230, or a material having high antibacterial such as copper, for example, be used as a material for forming the frame body 230.

In mounting the ultraviolet ray blocking elastic bodies 210, 220 on the frame body 230, the respective peripheral edge portions 210a, 220a of the ultraviolet ray blocking elastic bodies 210, 220 are supported by the receiving grooves 231, 232 of the frame body 230 such that the cuts C formed in the ultraviolet ray blocking elastic bodies 210, 220 are displaced from each other along the plate surfaces of the ultraviolet ray blocking elastic bodies 210, 220. In other words, when the ultraviolet ray blocking elastic bodies 210, 220 are viewed in a plan view, the respective peripheral edge portions 210a, 220a are supported by the receiving grooves 231, 232 of the frame body 230 in a state where the cuts C formed in the first ultraviolet ray blocking elastic body 210 and the cuts C formed in the second ultraviolet ray blocking elastic body 220 do not agree with each other.

In this case, the cuts C formed in the ultraviolet ray blocking elastic bodies 210, 220 are formed with an angle of 36 degrees. Accordingly, for example, as shown in FIG. 4A, the first ultraviolet ray blocking elastic body 210 and the second ultraviolet ray blocking elastic body 220 are supported by the receiving grooves 231, 232 of the frame body 230 such that the cuts C (indicated by a solid line) formed in the first ultraviolet ray blocking elastic body 210 and the cuts C (indicated by a broken line) formed in the second ultraviolet ray blocking elastic body 220 respectively have "displacement" of 18 degrees.

In FIG. 4A and FIG. 4B, "displacement" between the cuts C formed in the first ultraviolet ray blocking elastic body 210 and the cuts C formed in the second ultraviolet ray blocking elastic body 220 is set to 18 degrees. However, such "displacement" is not limited to 18 degrees. However, it is preferable that "displacement" between the cuts C formed in the first ultraviolet ray blocking elastic body 210 and the cuts C formed in the second ultraviolet ray blocking elastic body 220 be large and hence, the maximum "displacement" be set to 18 degrees.

In the ultraviolet ray irradiation device 10A according to the embodiment 1, the first ultraviolet ray blocking elastic body 210 and the second ultraviolet ray blocking elastic body 220 are stacked in a state where the first ultraviolet ray blocking elastic body 210 and the second ultraviolet ray blocking elastic body 220 are disposed close to each other. A distance d (distance along a z direction) between the first ultraviolet ray blocking elastic body 210 and the second ultraviolet ray blocking elastic body 220 is set to a slight distance (for example, approximately 1 mm to 5 mm). However, such a distance is not particularly limited, and may be suitably set to an optimum distance. The first ultraviolet ray blocking elastic body 210 and the second ultraviolet ray blocking elastic body 220 may be brought into contact with each other. By stacking the first ultraviolet ray blocking elastic body 210 and the second ultraviolet ray blocking elastic body 220 in a state where the first ultraviolet ray blocking elastic body 210 and the second ultraviolet ray blocking elastic body 220 are disposed close to each other or in a state where the first ultraviolet ray blocking elastic body 210 and the second ultraviolet ray blocking elastic body 220 are disposed in a contact state, a size of the ultraviolet ray irradiation device 10A in a height direction (a direction along which a hand on which the glove G is mounted is inserted) can be reduced.

As described above, the ultraviolet ray blocking elastic bodies 210, 220 are mounted on the frame body 230 by making the frame body 230 support the respective peripheral edge portions 210a, 220a of the ultraviolet ray blocking elastic bodies 210, 220. In mounting the ultraviolet ray blocking elastic bodies 210, 220 on the frame body 230, it may be possible to adhere the peripheral edge portions 210a, 220a of the ultraviolet ray blocking elastic bodies 210, 220 to the receiving grooves 231, 232 of the frame body 230 using an adhesive agent, or a structure may be adopted where the peripheral edge portions 210a, 220a of the ultraviolet ray blocking elastic bodies 210, 220 can be detachably mounted in the receiving grooves 231, 232 of the frame body 230.

In the case where the structure is adopted where the ultraviolet ray blocking elastic bodies 210, 220 can be detachably mounted on the frame body 230, it is preferable that the structure be formed such that the ultraviolet ray blocking elastic bodies 210, 220 can be easily inserted into the receiving grooves 231, 232 of the frame body 230 and cannot be easily removed by withdrawing from the receiving grooves 231, 232 of the frame body 230 after the insertion. For examples, a structure may be exemplified where projections having elasticity are mounted on surfaces of the peripheral edge portions 210a, 220a of the ultraviolet ray blocking elastic bodies 210, 220, and recessed portions with which the projections engage are formed on the receiving grooves 231, 232 of the frame body 230. The mounting structure for mounting the ultraviolet ray blocking elastic bodies 210, 220 on the frame body 230 is not particularly limited, and various structures can be adopted.

Figure 5:
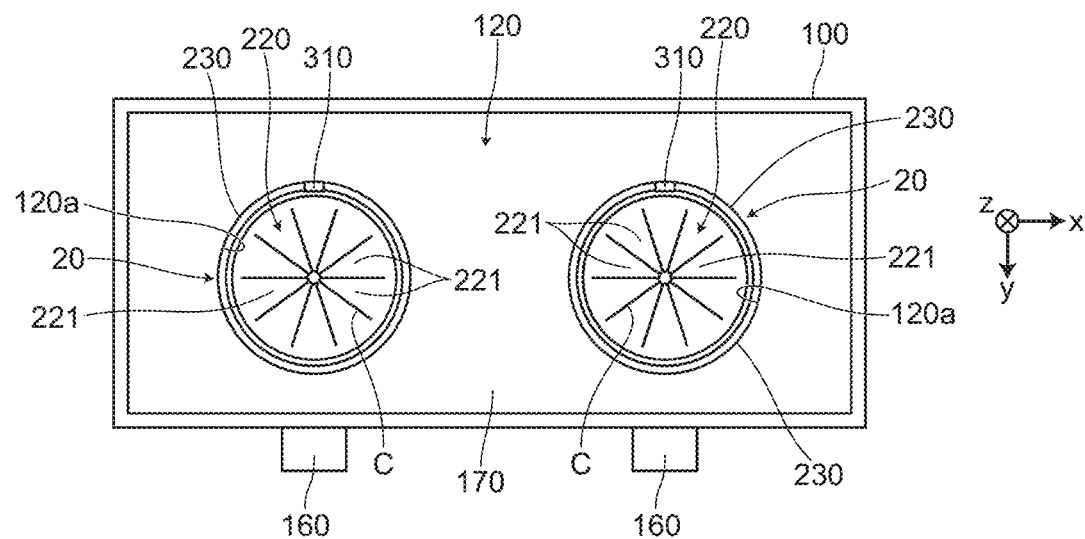
FIG. 5 is a plan view of the ultraviolet ray irradiation device 10A according to the embodiment 1 as viewed from below along a z axis.

FIG. 5 is a plan view of the ultraviolet ray irradiation device 10A according to the embodiment 1 as viewed from below along a z axis. As shown in FIG. 5, when the ultraviolet ray irradiation device 10A according to the embodiment 1 is viewed from below along the z axis, two second ultraviolet ray blocking elastic bodies 220 mounted on the frame body 230 are disposed side by side with a predetermined distance therebetween corresponding to both left and right hands of an operator W. The predetermined distance between two second ultraviolet ray blocking elastic bodies 220 is not particularly limited. However, it is preferable to set the distance which allows an operator to easily insert both left and right hands into the ultraviolet ray irradiation device 10A in a natural state.

Since the ultraviolet ray blocking elastic bodies 210, 220 are mounted on the frame body 230 as shown in FIG. 4A, FIG. 4B and FIG. 5, when an operator inserts a hand on which the glove G is mounted into the ultraviolet ray irradiation device 10A through the insertion openings 120 (see FIG. 2) positioned at a lower end of the sterilization chamber housing 100 (see FIG. 1 and FIG. 2), the hand on which the glove G is mounted can penetrate the respective elastic members 221 of the second ultraviolet ray blocking elastic body 220 and the respective elastic members 211 of the first ultraviolet ray blocking elastic body 210 respectively. In performing such an operation, it is preferable for the operator W to insert a hand on which the glove G is mounted into the insertion openings 120 "by putting fingers together in a tapered shape".

Figure 6:
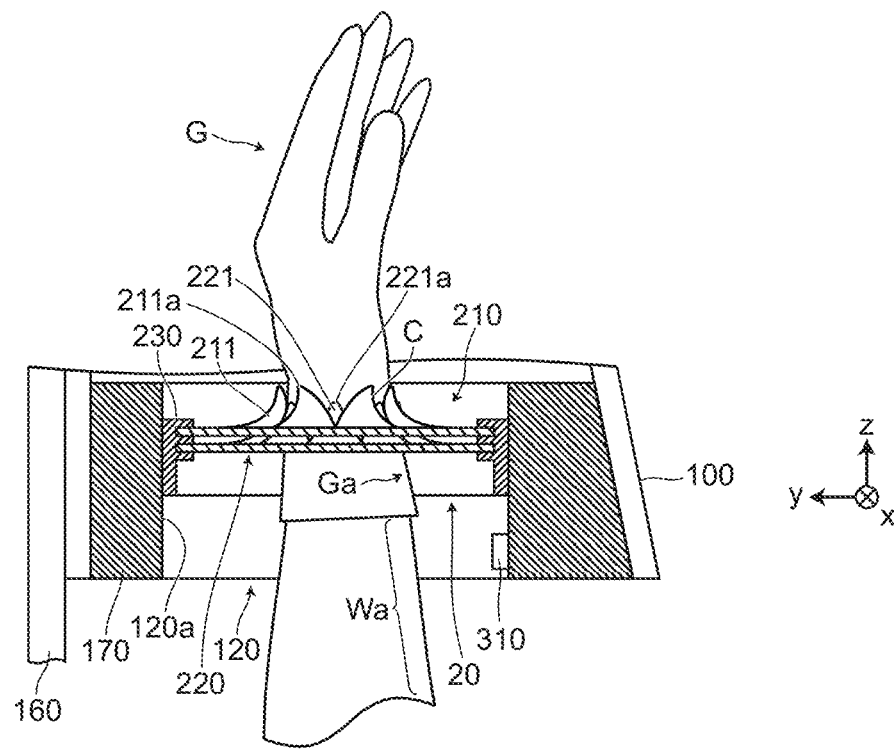
FIG. 6 is a view showing a state where a hand on which the glove G is mounted penetrates respective elastic members 221 of a second ultraviolet ray blocking elastic body 220 and respective elastic members 211 of the first ultraviolet ray blocking elastic body 210.

FIG. 6 is a view showing a state where a hand on which the glove G is mounted penetrates the respective elastic members 221 of the second ultraviolet ray blocking elastic body 220 and the respective elastic members 211 of the first ultraviolet ray blocking elastic body 210. In FIG. 6, a left hand of the operator W is shown. In the respective elastic members 211, 221 which the ultraviolet ray blocking elastic bodies 210, 220 have, the respective distal end portions 211a, 221a of the respective elastic members 211, 221 form free ends. Accordingly, the hand on which the glove G is mounted can penetrate the respective elastic members 221 of the second ultraviolet ray blocking elastic body 220 and the respective elastic members 211 of the first ultraviolet ray blocking elastic body 210 respectively.

To be more specific, when the operator inserts a hand on which the glove G is mounted into the sterilization chamber housing 100 through the insertion opening 120 positioned on a lower end of the sterilization chamber housing 100, the respective elastic members 221, 211 maintain a state where the elastic members 221, 211 are brought into close contact with a surface of the glove G due to a restoring force which intends to restore an original state while being bent by pushing in an upward direction (a direction that the hand on which the glove G is mounted advances) along with the movement of the hand on which the glove G is mounted. As shown in FIG. 6, when the hand on which the glove G is mounted further advances in the upward direction, the hand on which the glove G is mounted penetrates the ultraviolet ray blocking elastic bodies 210, 220. Then, when the hand on which the glove G is mounted is brought into a state where the hand is inserted into the sterilization chamber 110 by a predetermined depth (a state where the hand is inserted into a depth which enables appropriate sterilization in the sterilization chamber 110), the respective elastic members 211, 221 of the respective ultraviolet ray blocking elastic bodies surround a periphery of a wrist portion Ga of the glove G in a state where the respective elastic members 211, 221 are brought into close contact with the wrist portion Ga of the glove G.

At this stage of the operation, the cuts C of the first ultraviolet ray blocking elastic body 210 and the cuts C of the second ultraviolet ray blocking elastic body 220 exist at positions displaced from each other by 18 degrees. Accordingly, the respective elastic members 221 of the second ultraviolet ray blocking elastic body 220 exist at positions of the respective cuts C of the first ultraviolet ray blocking elastic body 210, and the respective elastic members 211 of the first ultraviolet ray blocking elastic body 210 exist at positions of the respective cuts C of the second ultraviolet ray blocking elastic body 220.

Accordingly, the wrist portion Ga of the glove G is brought into a state where the wrist portion Ga is covered by the respective elastic members 211 of the first ultraviolet ray blocking elastic body 210 and the respective elastic members 221 of the second ultraviolet ray blocking elastic body 210 without any gap. Therefore, ultraviolet rays which the ultraviolet ray irradiation lamps 130 irradiate can be blocked with certainty and hence, it is possible to prevent with certainty the irradiation of the ultraviolet rays to a side behind the ultraviolet ray blocking elastic bodies 210, 220 (the bare skin region Wa of the left hand of the operator W).

The description is made with respect to only the left hand out of both left and right hands of the operator W heretofore. However, the same goes for the right hand. That is, the wrist portion Ga of the glove G mounted on the right hand of the operator W is brought into a state where the wrist portion Ga is covered by the respective elastic members 211 of the first ultraviolet ray blocking elastic body 210 and the respective elastic members 221 of the second ultraviolet ray blocking elastic body 220 without any gap. Accordingly, ultraviolet rays which the ultraviolet ray irradiation lamps 130 irradiate can be blocked with certainty and hence, it is possible to prevent with certainty the irradiation of the ultraviolet rays to a side behind the ultraviolet ray blocking elastic bodies 210, 220 (the bare skin region Wa of the right hand of the operator W).

Subsequently, the bare skin detection unit 310 which is an insertion depth detection unit is described. The bare skin detection unit 310 is disposed at a position where a bare skin region Wa right below the wrist portion Ga of the glove G can be detected when the hand on which the glove G is mounted is brought into a state where the hand is inserted into the sterilization chamber 110 by a predetermined depth (for example, a state shown in FIG. 6). To be more specific, the bare skin detection unit 310 is mounted on the respective peripheral edge portions 120*a* of the pair of insertion openings 120 at a position on an entrance side of the insertion opening 120 formed in the sterilization chamber housing member 170 with respect to the ultraviolet ray blocking elastic bodies 210, 220. The bare skin detection unit 310 outputs a bare skin detection signal as an insertion depth detection signal when the bare skin detection unit 310 detects the bare skin region Wa right below the wrist portion Ga of the glove G.

By mounting the bare skin detection unit 310 at the above-mentioned position, when the hand on which the glove G is mounted is brought into a state where the hand is inserted into the sterilization chamber 110 by a predetermined depth (see FIG. 6), the bare skin detection unit 310 detects the bare skin region Wa right below the wrist portion Ga of the glove G, and outputs a bare skin detection signal.

With respect to the hand on which the glove G is mounted, "a state where the hand is inserted into the sterilization chamber 110 by a predetermined depth" means, as described previously, a state where the hand on which the glove G is mounted is inserted into the sterilization chamber 110 to a depth which enables appropriate sterilization. Accordingly, when a bare skin detection signal is outputted from the bare skin detection unit 310, this condition indicates that the hand on which the glove G is mounted is inserted into the sterilization chamber 110 to a depth which enables appropriate sterilization.

Figure 7:
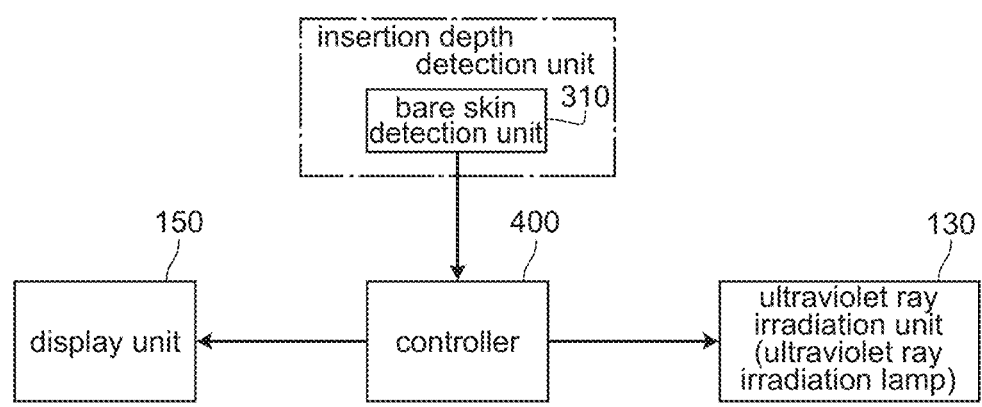
FIG. 7 is a view for describing a control of the ultraviolet ray irradiation device 10A according to the embodiment 1.

Next, the controller 400 is described with reference to FIG. 7. The controller 400 performs an overall control of the ultraviolet ray irradiation device 10A according to the embodiment 1. Controls relating to the description of the ultraviolet ray irradiation device 10A according to the embodiment 1 are described hereinafter. In this case, controls which the controller 400 performs include, as shown in FIG. 7, a control performed for turning on or off the ultraviolet ray irradiation lamps 130 and a control performed for displaying whether or not a hand on which the glove G is mounted is inserted into the sterilization chamber 110 by a predetermined depth on the display unit 150. These controls are performed based on a bare skin detection signal outputted from the bare skin detection unit 310.

That is, when the hand on which the glove G is mounted is brought into a state shown in FIG. 6, the bare skin detection unit 310 detects the bare skin region Wa, a bare skin detection signal is transmitted to the controller 400. The controller 400, based on the bare skin detection signal transmitted from the bare skin detection unit 310, transmits a signal which indicates the insertion of the hand on which the glove G is mounted into the sterilization chamber 110 by a predetermined depth (a depth which enables appropriate sterilization) to the display unit 150.

The display unit 150 performs a display indicating that the hand on which the glove G is mounted is inserted into the sterilization chamber 110 by the predetermined depth (depth which enables appropriate sterilization). As another display example which the display unit 150 performs, for example, the insertion of the hand is notified by turning on a blue lamp or generating a voice. Accordingly, an operator W knows the insertion of the hand on which the glove G is mounted by the depth which enables the appropriate sterilization. Further, the operator W can visually recognize an appearance in which the hand on which the glove G is mounted is inserted into the sterilization chamber 110 through slits S1, S2 (see FIG. 1). It is preferable that the operator W opens respective fingers of the hand on which the glove G is mounted after the hand is inserted into the sterilization chamber 110.

In this manner, in a state where the hand on which the glove G is mounted is inserted into the sterilization chamber 110 by a predetermined depth (depth which enables appropriate sterilization), the controller 400 turns on the ultraviolet ray irradiation lamps 130. When the ultraviolet ray irradiation lamps 130 are turned on, a surface of the glove G can be sterilized. In such an operation, as shown in FIG. 6, the wrist portion Ga of the glove G is brought into a state where the wrist portion Ga is covered by the respective elastic members 211 of the first ultraviolet ray blocking elastic body 210 and the respective elastic members 221 of the second ultraviolet ray blocking elastic body 220 without any gap.

Accordingly, ultraviolet rays which the ultraviolet ray irradiation lamps 130 irradiate can be blocked with certainty and hence, it is possible to prevent with certainty the irradiation of the ultraviolet rays to a side behind the ultraviolet ray blocking elastic bodies 210, 220 (the bare skin region Wa of the left hand of the operator W). Further, it is possible to prevent with certainty the irradiation of the ultraviolet rays not only to the operator W who is performing sterilization at the moment but also to operators around such an operator W. Then, the controller 400 turns off the ultraviolet ray irradiation lamps 130.

It is preferable that the controller 400 perform a preheating control at a stage before the ultraviolet ray irradiation lamps 130 are turned on. In this case, an operator detection unit (not shown in the drawings) which detects the presence of an operator W who performs disinfection at the moment in front of the ultraviolet ray irradiation device 10A according to the embodiment 1 may be mounted on a front surface of the sterilization chamber housing 100. With the provision of the operator detection unit, when the operator W faces the sterilization chamber housing 100 (see FIG. 2), the operator detection unit detects the presence of the operator W, and it is possible to preheat the ultraviolet ray irradiation lamps 130 by making use of a time period (for example, a time period of approximately 2 seconds) from a point of time that the operator W is detected to a point of time that the bare skin detection unit 310 detects the bare skin region Wa.

In this manner, by performing preheating of approximately 2 seconds before the ultraviolet ray irradiation lamps 130 are turned on, a rise time at the time of turning on the ultraviolet ray irradiation lamps 130 can be shortened. Accordingly, an efficient sterilization operation can be performed thus extending a lifetime of the ultraviolet ray irradiation lamps 130.

As described above, in the ultraviolet ray irradiation device 10A according to the embodiment 1, when the hand on which the glove G is mounted is inserted into the respective elastic members 221 of the second ultraviolet ray blocking elastic body through the insertion opening 120, the hand on which the glove G is mounted penetrates the respective elastic members 221 of the second ultraviolet ray blocking elastic body 220 and the respective elastic members 211 of the first ultraviolet ray blocking elastic body 220. Then, when the hand on which the glove G is mounted is brought into a state where the hand is inserted into the sterilization chamber 110 by a predetermined depth, the respective elastic members 211, 221 of the ultraviolet ray blocking elastic bodies 210, 220 surround a periphery of a wrist portion Ga of the glove G in a state where the respective elastic members 211, 221 are brought into close contact with the wrist portion Ga of the glove G.

At this stage of the operation, the cuts C of the first ultraviolet ray blocking elastic body 210 and the cuts C of the second ultraviolet ray blocking elastic body 220 exist at positions displaced from each other by 18 degrees. Accordingly, the respective elastic members 221 of the second ultraviolet ray blocking elastic body 220 exist at positions of the respective cuts C of the first ultraviolet ray blocking elastic body 210, and the respective elastic members 211 of the first ultraviolet ray blocking elastic body 210 exist at positions of the respective cuts C of the second ultraviolet ray blocking elastic body 220. Therefore, ultraviolet rays which the ultraviolet ray irradiation lamps 130 irradiate can be blocked with certainty and hence, it is possible to prevent with certainty the irradiation of the ultraviolet rays to a side behind the ultraviolet ray blocking elastic bodies 210, 220 (the bare skin region Wa of the left hand of the operator W).

Embodiment 2

Subsequently, an ultraviolet ray irradiation device 10B according to an embodiment 2 is described. The external appearance configuration of the ultraviolet ray irradiation device 10B according to the embodiment 2 is equal to the external appearance configuration of the ultraviolet ray irradiation device 10A according to the embodiment 1. Accordingly, when it is necessary to describe the external appearance configuration of the ultraviolet ray irradiation device 10B according to the embodiment 2, the description is made with reference to FIG. 1. The cross-sectional view of the ultraviolet ray irradiation device 10A shown in FIG. 1 can be used also as a cross-sectional view of the ultraviolet ray irradiation device 10B according to the embodiment 2 and hence, when it is necessary to describe the cross-sectional configuration of the ultraviolet ray irradiation device 10B according to the embodiment 2, the description is made with reference to FIG. 2.

A point which makes the ultraviolet ray irradiation device 10B according to the embodiment 2 differ from the ultraviolet ray irradiation device 10A according to the embodiment 1 lies in an ultraviolet ray blocking elastic body. A first ultraviolet ray blocking elastic body (first ultraviolet ray blocking elastic body 250) and a second ultraviolet ray blocking elastic body (second ultraviolet ray blocking elastic body 260) used in the ultraviolet ray irradiation device 10B according to the embodiment 2 have an oblong planar shape. Also in the ultraviolet ray irradiation device 10B according to the embodiment 2, in indicating both the first ultraviolet ray blocking elastic body 250 and the second ultraviolet ray blocking elastic body 260, the expression "ultraviolet ray blocking elastic bodies 250, 260" or "respective ultraviolet ray blocking elastic bodies 250, 260" may also be adopted.

Figure 8A:
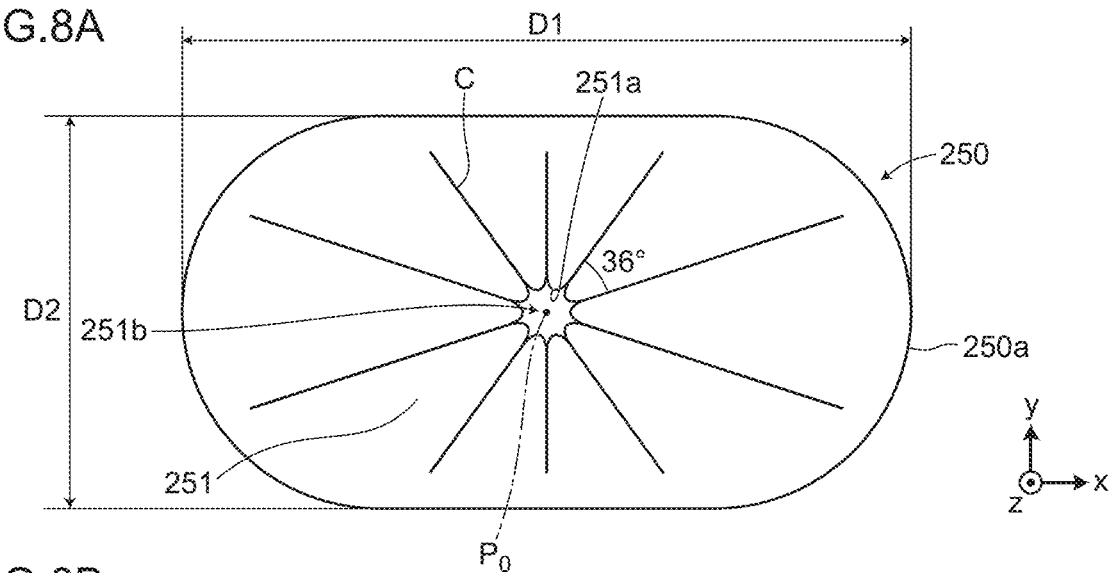
FIG. 8A to FIG. 8C are views for describing a first ultraviolet ray blocking elastic body 250 and a second ultraviolet ray blocking elastic body 260 used in an ultraviolet ray irradiation device 10B according to an embodiment 2.
Figure 8B:
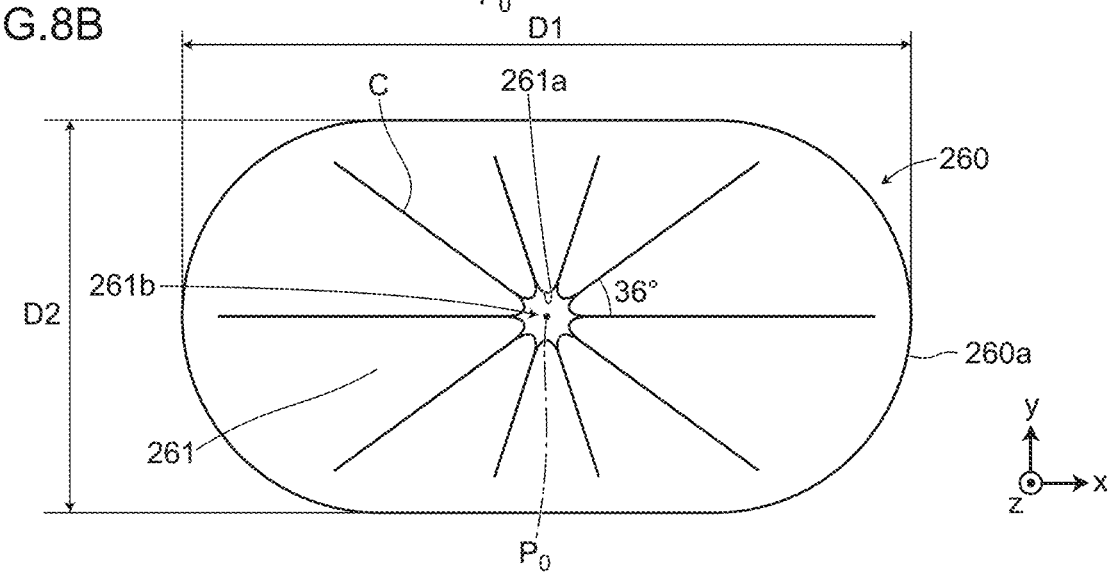
Figure 8C:
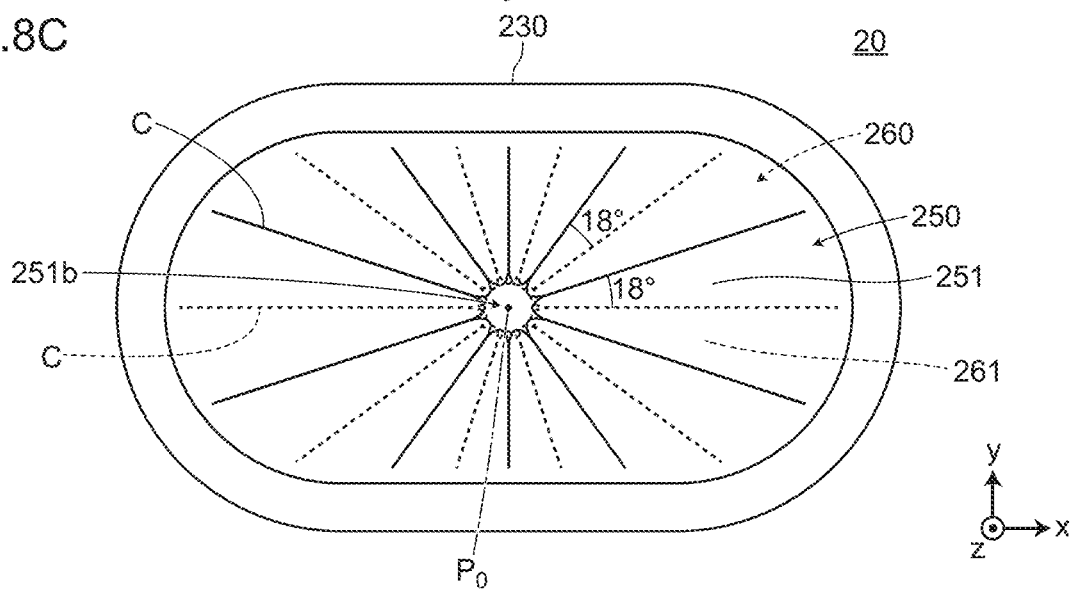

FIG. 8A to FIG. 8C are views for describing the first ultraviolet ray blocking elastic body 250 and the second ultraviolet ray blocking elastic body 260 used in the ultraviolet ray irradiation device 10B according to the embodiment 2. FIG. 8A is a plan view showing the first ultraviolet ray blocking elastic body 250, FIG. 8B is a plan view showing the second ultraviolet ray blocking elastic body 260, and FIG. 8C is a plan view showing an appearance where the first ultraviolet ray blocking elastic body 250 and the second ultraviolet ray blocking elastic body 260 are mounted on a frame body 230 in a stacked state.

The ultraviolet ray blocking elastic bodies 250, 260 each have a major diameter D1 of approximately 120 mm to 180 mm, a minor diameter D2 of approximately 100 mm to 140 mm, and a thickness of approximately 0.5 mm to 3 mm. However, the sizes of the ultraviolet ray blocking elastic bodies 250, 260 are not limited to these sizes.

As shown in FIG. 8A, a plurality of cuts C are formed in the first ultraviolet ray blocking elastic body 250 such that the plurality of cuts C linearly and radially extend from a predetermined position of the first ultraviolet ray blocking elastic body 250 (assuming the center Po of the first ultraviolet ray blocking elastic body 250) toward a peripheral edge portion 250a of the first ultraviolet ray blocking elastic body 250. The cuts C do not reach the peripheral edge portion 250a.

As shown in FIG. 8B, a plurality of cuts C are formed in the second ultraviolet ray blocking elastic body 260 such that the plurality of cuts C linearly and radially extend from a predetermined position of the second ultraviolet ray blocking elastic body 260 (assuming the center Po of the second ultraviolet ray blocking elastic body 260) toward a peripheral edge portion 260a of the second ultraviolet ray blocking elastic body 260. The cuts C do not reach the peripheral edge portion 260a also in the second ultraviolet ray blocking elastic body 260.

In the ultraviolet ray blocking elastic bodies 250, 260, in the same manner as the ultraviolet ray blocking elastic bodies 210, 220 described in the embodiment 1, the number of cuts C is set to 10, and an angle made by the cuts C disposed adjacently to each other becomes 36 degrees. Accordingly, in the first ultraviolet ray blocking elastic body 250, 10 pieces of elastic members 251 each having a "wedge shape" having a narrow distal end are formed, wherein each elastic member 251 is formed between the respective cuts C disposed adjacently to each other. In the same manner as the first ultraviolet ray blocking elastic body 250, in the first ultraviolet ray blocking elastic body 260, 10 pieces of elastic members 261 each having a "wedge shape" having a narrow distal end are formed, wherein each elastic member 261 is formed between the respective cuts C disposed adjacently to each other. In the ultraviolet ray blocking elastic bodies 250, 260, lengths of the respective cuts C are lengths corresponding to distances to the peripheral edge portions 250a, 260a. That is, the longer distances from the center Po to the peripheral edge portions 250a, 260a are, the greater the lengths of the respective cuts C become.

With respect to 10 pieces of elastic members 251 (also expressed as respective elastic members 251) of the first ultraviolet ray blocking elastic body 250, an end portion 251a (assuming as a distal end portion 251a) on a center Po side forms a free end. In the same manner, with respect to pieces of elastic members 261 (also expressed as respective elastic members 261) of the second ultraviolet ray blocking elastic body 260, an end portion 261a (assuming as a distal end portion 261a) on the center Po side forms a free end.

With respect to each elastic member 251 of the first ultraviolet ray blocking elastic body 250, a sharpened distal end portion is cut away so as to form a rounded distal end portion 251a. In this manner, with respect to each elastic member 251 of the first ultraviolet ray blocking elastic body 250, the sharpened distal end portion is cut away. Accordingly, at the position where the respective distal end portions 251a of the respective elastic members 251 of the first ultraviolet ray blocking elastic members 250 marge, a space portion (penetration hole) 251b which is surrounded by the respective distal end portions 251a is formed.

In the same manner as the first ultraviolet ray blocking elastic body 250, with respect to each elastic member 261 of the second ultraviolet ray blocking elastic body 260, a sharpened distal end portion is cut away so as to form a rounded distal end portion 261a. In this manner, with respect to each elastic member 261 of the second ultraviolet ray blocking elastic body 260, the sharpened distal end portion is cut away. Accordingly, at the position where the respective distal end portions 261a of the respective elastic members 261 of the second ultraviolet ray blocking elastic bodies 260 marge, a space portion (penetration hole) 261b which is surrounded by the respective distal end portions 261a is formed.

The center of the space portion 251b surrounded by the respective distal end portions 251a of the respective elastic members 251 and the center of the space portion 261b surrounded by the respective distal end portions 261a of respective elastic members 261 are aligned with the center Po of the ultraviolet ray blocking elastic bodies 250, 260. The ultraviolet ray blocking elastic bodies 250, 260 having such a configuration are mounted on the frame body 230 in a stacked state (see FIG. 8C). Also in this case, the ultraviolet ray blocking unit 20 can be formed of the ultraviolet ray blocking elastic bodies 250 and the frame body 230.

In the ultraviolet ray irradiation device 10B according to the embodiment 2, the ultraviolet ray blocking elastic bodies 250, 260 are not formed in a circular shape but are formed in an elliptical shape and hence, in mounting the ultraviolet ray blocking elastic bodies 250, 260 on the frame body 230, the mounting positions of the ultraviolet ray blocking elastic bodies 250, 260 with respect to the frame body 230 are limited. Accordingly, it is necessary to form cuts C formed in the first ultraviolet ray blocking elastic body 250 and cuts C formed in the second ultraviolet ray blocking elastic body 260 so as to prevent the cuts C formed in the first ultraviolet ray blocking elastic body 250 and the cuts C formed in the second ultraviolet ray blocking elastic body 260 from being aligned with each other (to displace the positions of the cuts C formed in the first ultraviolet ray blocking elastic body 250 and the positions of the cuts C formed in the second ultraviolet ray blocking elastic body 260 from each other). In this case, the cuts C formed in the first ultraviolet ray blocking elastic body 250 and the cuts C formed in the second ultraviolet ray blocking elastic body 260 are displaced from each other by 18 degrees.

With such a configuration, when the first ultraviolet ray blocking elastic body 250 and the second ultraviolet ray blocking elastic body 260 are mounted on the frame body 230 in a stacked state, as shown in FIG. 8C, the cuts C (the cuts C indicted by a solid line) formed in the first ultraviolet ray blocking elastic body 250 and the cuts C (the cuts C indicated by a broken line) formed in the second ultraviolet ray blocking elastic body 260 exist at the positions displaced from each other by 18 degrees.

Figure 9:
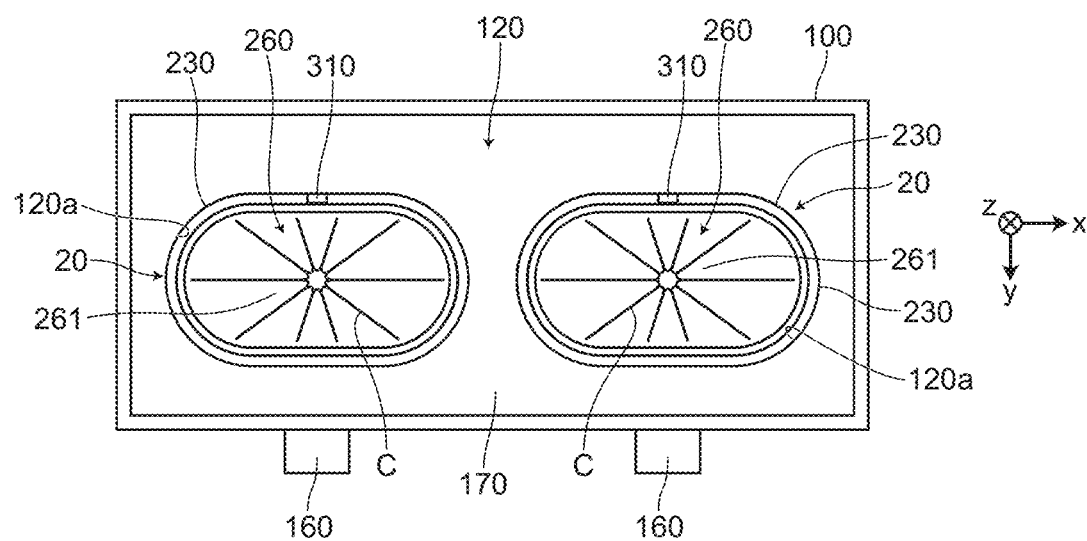
FIG. 9 is a plan view of the ultraviolet ray irradiation device 10B according to the embodiment 2 as viewed from below along a z axis.

FIG. 9 is a plan view of the ultraviolet ray irradiation device 10B according to the embodiment 2 as viewed from below along a z axis. As shown in FIG. 9, when the sterilization chamber housing 100 is viewed from below along the z axis, two second ultraviolet ray blocking elastic bodies 260 mounted on the frame body 230 are disposed side by side with a predetermined distance therebetween corresponding to both left and right hands of an operator. The distance between two second ultraviolet ray blocking elastic bodies 260 is not particularly limited. However, it is preferable to set the distance which allows the operator W to easily insert both left and right hands into the sterilization chamber housing 100 in a natural state.

In the same manner as the ultraviolet ray irradiation device 10A according to the embodiment 1, also in the ultraviolet ray irradiation device 10B according to the embodiment 2, the hand on which the glove G is mounted can penetrate the respective elastic members 251, 261 of the respective ultraviolet ray blocking elastic bodies 250, 260 (see FIG. 6). Then, when the hand on which the glove G is mounted is brought into a state where the hand is inserted into the sterilization chamber 110 by a predetermined depth, the respective elastic members 251, 261 of the ultraviolet ray blocking elastic bodies 250, 260 surround a periphery of a wrist portion Ga of the glove G in a state where the respective elastic members 251, 261 are brought into close contact with the wrist portion Ga of the glove G.

At this stage of the operation, the cuts C of the first ultraviolet ray blocking elastic body 250 and the cuts C of the second ultraviolet ray blocking elastic body 260 exist at positions displaced from each other by 18 degrees. Accordingly, the respective elastic members 251 of the second ultraviolet ray blocking elastic body 260 exist at positions of the respective cuts C of the first ultraviolet ray blocking elastic body 250, and the respective elastic members 261 of the first ultraviolet ray blocking elastic body 250 exist at positions of the respective cuts C of the second ultraviolet ray blocking elastic body 260. Therefore, also in the ultraviolet ray irradiation device 10B according to the embodiment 2, in the same manner as the ultraviolet ray irradiation device 10A according to the embodiment 1, the ultraviolet rays which the ultraviolet ray irradiation lamps 130 irradiate can be blocked with certainty and hence, it is possible to prevent with certainty the irradiation of the ultraviolet rays to a side behind the ultraviolet ray blocking elastic bodies 250, 260 (the bare skin region Wa of the left hand of the operator W).

In the ultraviolet ray irradiation device 10B according to the embodiment 2, the ultraviolet ray blocking elastic bodies 250, 260 have an oblong shape and hence, the respective elastic members 251, 261 through which the hand on which the glove G is mounted is inserted are elongated in the lateral direction (direction along the x axis). Accordingly, when each operator W inserts his/her hand on which the glove G is mounted into the sterilization chamber housing 100, it is unnecessary for the operator W to intentionally "putting fingers of the hand together in a tapered shape" and hence, the operator W can insert the hand on which the glove G is mounted in a natural form.

Modification of Ultraviolet Ray Irradiation Device 10B According to Embodiment 2

Figure 10A:
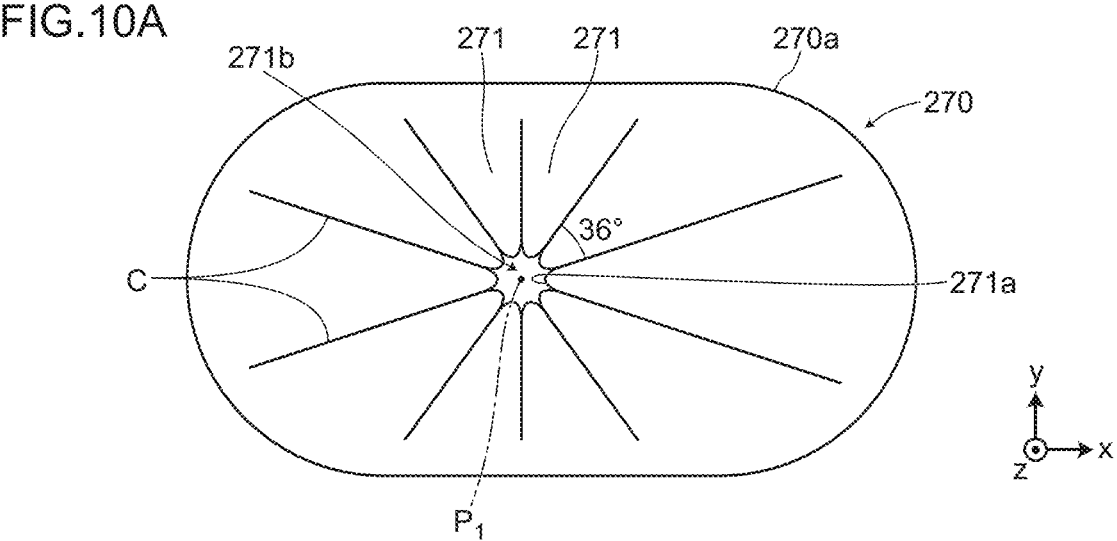
FIG. 10A to FIG. 10C are views for describing a first ultraviolet ray blocking elastic body 270 and a second ultraviolet ray blocking elastic body 280 used in a modification of the ultraviolet ray irradiation device 10B according to the embodiment 2.
Figure 10B:
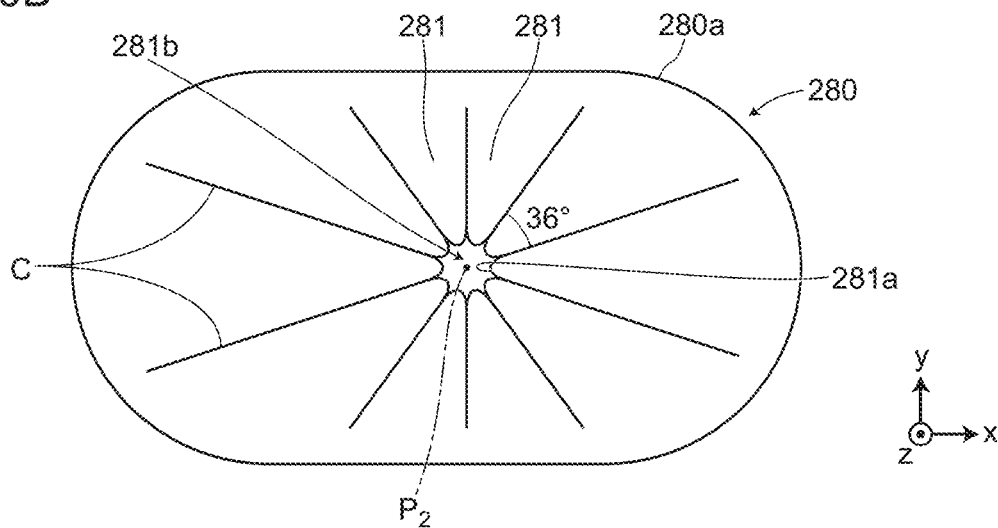
Figure 10C:
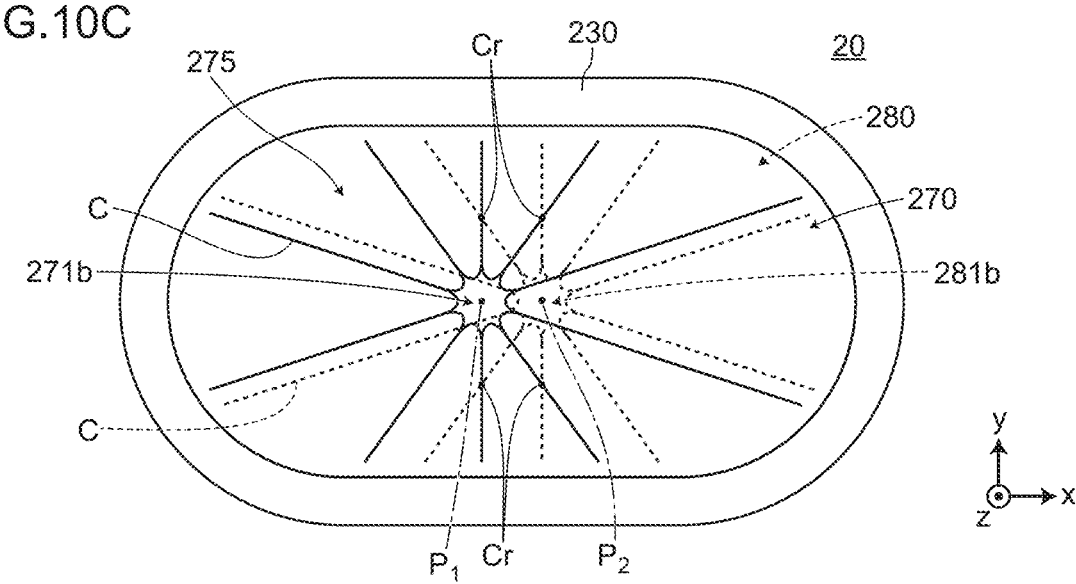

FIG. 10A to FIG. 10C are views for describing a first ultraviolet ray blocking elastic body 270 and a second ultraviolet ray blocking elastic body 280 used in a modification of the ultraviolet ray irradiation device 10B according to the embodiment 2. FIG. 10A is a plan view showing the first ultraviolet ray blocking elastic body 270, FIG. 10B is a plan view showing the second ultraviolet ray blocking elastic body 280. FIG. 10C is a plan view showing an appearance where the first ultraviolet ray blocking elastic body 270 and the second ultraviolet ray blocking elastic body 280 are mounted on a frame body 230 in a stacked state.

In the above-mentioned ultraviolet ray irradiation device 10B according to the embodiment 2, as shown in FIG. 8C, both of the position where respective distal end portions 251a of respective elastic members 251 of the first ultraviolet ray blocking elastic body 250 marge (the position where a space portion 251b is formed) and the position where respective distal end portions 261a of respective elastic members 261 of the second ultraviolet ray blocking elastic body 260 marge (the position where a space portion 261b is formed) exist at the same position (the center Po of the ultraviolet ray blocking elastic bodies 250, 260).

On the other hand, in the modification of the ultraviolet ray irradiation device 10B according to the embodiment 2, as shown in FIG. 10A to FIG. 10C, the position where respective distal end portions 271a of respective elastic members 271 of the first ultraviolet ray blocking elastic body 270 marge (the position of a space portion 271b surrounded by the respective distal end portions 271a) and the position where respective distal end portions 281a of respective elastic members 281 of the second ultraviolet ray blocking elastic body 280 marge (the position of a space portion 281b surrounded by the respective distal end portions 281a) exist at positions spaced apart from each other along major diameters of the ultraviolet ray blocking elastic bodies 270, 280.

That is, assuming the center of the space portion 271b surrounded by the respective distal end portions 271a as P1 and the center of the space portion 281b surrounded by the respective distal end portions 281a as P2, the center P1 of the space portion 271b and the center P2 of the space portion 281b exist at the positions spaced apart from each other along the respective major diameters of the ultraviolet ray blocking elastic bodies 270, 280. It is preferable that the distance between the center P1 of the space portion 271b and the center P2 of the space portion 281b be approximately 3 mm to 20 mm. In the modification of the ultraviolet ray irradiation device 10B according to the embodiment 2, as shown in FIG. 10A and FIG. 10B, with respect to the cuts C of the first ultraviolet ray blocking elastic body 270 and cuts C of the second ultraviolet ray blocking elastic body 280, assume that the respective cuts C are formed without displacement of 18 degrees from each other.

In this manner, in the modification of the ultraviolet ray irradiation device 10B according to the embodiment 2, the position where the respective distal end portions 271a of the respective elastic members 271 of the first ultraviolet ray blocking elastic body 270 marge (the position of the space portion 271b surrounded by the respective distal end portions 271a) and the position where the respective distal end portions 281a of the respective elastic members 281 of the second ultraviolet ray blocking elastic body 280 marge (the position of the space portion 281b surrounded by the respective distal end portions 281a) exist at positions spaced apart from each other along the major diameters of the ultraviolet ray blocking elastic bodies 270, 280. In this modification, in the same manner as the ultraviolet ray irradiation device 10B according to the embodiment 2, the hand on which the glove G is mounted can penetrate the elastic members 271, 281 each formed between the cuts C disposed adjacently to each other.

Accordingly, in the same manner as the ultraviolet ray irradiation device 10B according to the embodiment 2, when the hand on which the glove G is mounted is brought into a state where the hand is inserted into the sterilization chamber 110 by a predetermined depth, the respective elastic members 271, 281 of the ultraviolet ray blocking elastic bodies 270, 280 surround a periphery of a wrist portion Ga of the glove G in a state where the respective elastic members 271, 281 are brought into close contact with the wrist portion Ga of the glove G.

In this case, there exist a plurality of intersecting portions Cr where the cuts C of the first ultraviolet ray blocking elastic body 270 and the cuts C of the second ultraviolet ray blocking elastic body 280 intersect with each other (see FIG. 10C). However, by further stacking a third ultraviolet ray blocking elastic body having elastic members which can cover the intersecting portions Cr, it is possible to block with certainty ultraviolet rays which the ultraviolet ray irradiation lamps 130.

Figure 11:
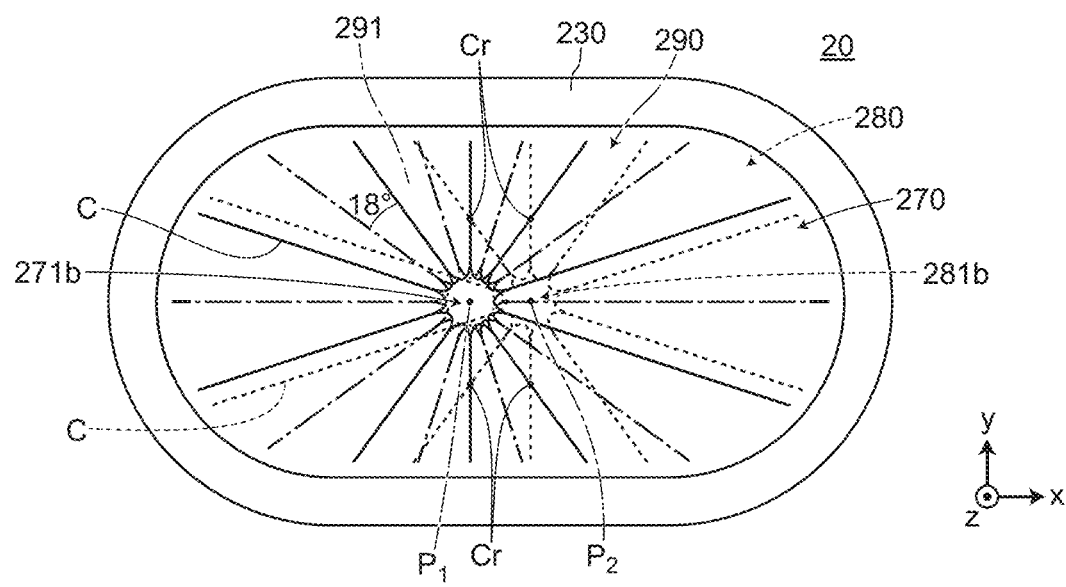
FIG. 11 is a view showing an example where a third ultraviolet ray blocking elastic body 290 having elastic members which can cover an intersecting portion Cr is further stacked.

FIG. 11 is a view showing an example where the third ultraviolet ray blocking elastic body which having the elastic members which can cover the intersecting portions Cr is further stacked. As shown in FIG. 11, the third ultraviolet ray blocking elastic body 290 having 10 pieces of elastic members 291 formed by cuts C (cuts indicated by a chain line) which are displaced by 18 degrees, for example, from the cuts C (cuts indicated by a solid line) of 10 pieces of the first ultraviolet ray blocking elastic body 270 is stacked on the first ultraviolet ray blocking elastic body 270. With such a configuration, the respective elastic members 291 (the elastic members 291 formed by the cuts C indicated by a chain line) of the third ultraviolet ray blocking elastic body 290 cover the intersecting portions Cr. Accordingly, ultraviolet rays which the ultraviolet ray irradiation lamps 130 irradiate can be blocked with certainty. The center of a space portion 291b of the third ultraviolet ray blocking elastic body 290 is located at the same position as the center P1 of the space portion 271b of the first ultraviolet ray blocking elastic body 270.

The configuration where the position at which the respective distal end portions 271a of the respective elastic members 271 of the first ultraviolet ray blocking elastic body 270 merge and the position at which the respective distal end portions 281a of the respective elastic members 281 of the second ultraviolet ray blocking elastic body 280 merge exist at the positions spaced apart from each other in major diameters of the ultraviolet ray blocking elastic bodies 270, 280 is also applicable to the ultraviolet ray irradiation device 10A according to the embodiment 1.

Embodiment 3

Figure 12:
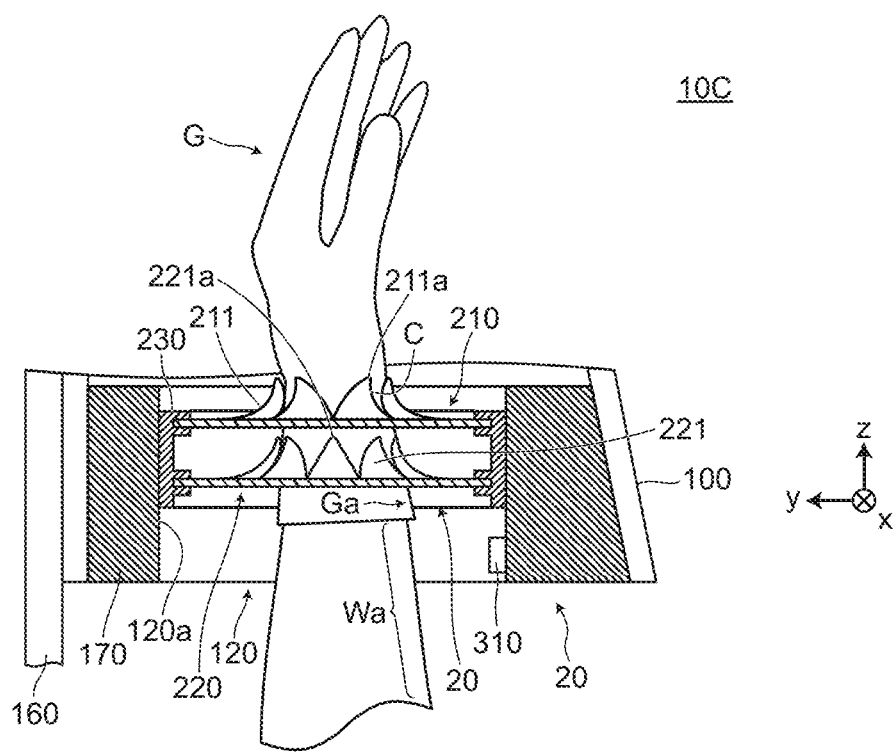
FIG. 12 is a view for describing an ultraviolet ray irradiation device 10C according to an embodiment 3.

FIG. 12 is a view for describing an ultraviolet ray irradiation device 10C according to an embodiment 3.

The ultraviolet ray irradiation device 10C according to the embodiment 3 differs from the above-mentioned ultraviolet ray irradiation device 10A according to the embodiment 1 with respect to a distance between a first ultraviolet ray blocking elastic body 210 and a second ultraviolet ray blocking elastic body 220 in a state where the first ultraviolet ray blocking elastic body 210 and the second ultraviolet ray blocking elastic body 220 are mounted on the frame body 230.

That is, in the ultraviolet ray irradiation device 10A according to the embodiment 1, the first ultraviolet ray blocking elastic body 210 and the second ultraviolet ray blocking elastic body 220 are mounted on the frame body 230 in a state where the first ultraviolet ray blocking elastic body 210 and the second ultraviolet ray blocking elastic body 220 are disposed adjacently to each other. On the other hand, in the ultraviolet ray irradiation device 10C according to the embodiment 3, a first ultraviolet ray blocking elastic body 210 and a second ultraviolet ray blocking elastic body 220 are mounted on a frame body 230 in a state where the first ultraviolet ray blocking elastic body 210 and the second ultraviolet ray blocking elastic body 220 are spaced apart from each other by a predetermined distance.

In this embodiment, to be more specific, "predetermined distance" is preferably be a distance by which, when a hand on which the glove G is mounted penetrates the second ultraviolet ray blocking elastic body 220 and the first ultraviolet ray blocking elastic body 210 so that respective elastic members 221 of the second ultraviolet ray blocking elastic body 220 are brought into an upwardly pushed and bent state, the respective elastic members 221 which are upwardly pushed and bent are not brought into contact with the respective elastic members 211 of the first ultraviolet ray blocking elastic body 210 or are slightly brought into contact with the respective elastic members 211 of the first ultraviolet ray blocking elastic body 210 (see FIG. 12).

In the ultraviolet ray irradiation device 10C according to the embodiment 3, the distance between the first ultraviolet ray blocking elastic body 210 and second ultraviolet ray blocking elastic body 220 is set in this manner. Accordingly, when a hand on which the glove G is mounted penetrates the second ultraviolet ray blocking elastic body 210, the respective elastic members 221 of the second ultraviolet ray blocking elastic body 220 are not brought into contact with the respective elastic members 211 of the first ultraviolet ray blocking elastic body 210 or are slightly brought into contact with the respective elastic members 211 of the first ultraviolet ray blocking elastic body 210. Therefore, the respective elastic members 221 of the second ultraviolet ray blocking elastic body 220 and the respective elastic members 211 of the first ultraviolet ray blocking elastic body 210 do not overlap with each other, or even when the respective elastic members 221 of the second ultraviolet ray blocking elastic body 220 and the respective elastic members 211 of the first ultraviolet ray blocking elastic body 210 overlap with each other, an overlapping portion is a narrow range.

With such configuration, the respective elastic members 221 of the second ultraviolet ray blocking elastic body 220 and the respective elastic members 211 of the first ultraviolet ray blocking elastic body 210 minimally interfere with each other. Accordingly, for example, it is possible to prevent the occurrence of a state where the respective elastic members 221 of the second ultraviolet ray blocking elastic body 220 and the respective elastic members 211 of the first ultraviolet ray blocking elastic body 210 are brought into close contact with each other and become minimally separable from each other. So, the penetration of a hand on which the glove G is mounted becomes easy, and the drawing out of the penetrating hand (hand on which the glove G is mounted) also becomes easy. Therefore, the insertion of a hand on which the glove G is mounted into the sterilization chamber 110 and the removal of the hand on which the glove G is mounted from the sterilization chamber 110 can be performed smoothly.

The configuration where the first ultraviolet ray blocking elastic body 210 and the second ultraviolet ray blocking elastic body 220 are mounted on the frame body 230 in a state where the first ultraviolet ray blocking elastic body 210 and the second ultraviolet ray blocking elastic body 220 are spaced apart from each other with a predetermined distance therebetween is also applicable to the ultraviolet ray irradiation device 10B according to the embodiment 2 and ultraviolet ray irradiation device 10B according to the modification of the embodiment 2.

Embodiment of Ultraviolet Ray Blocking Unit

Subsequently, an ultraviolet ray blocking unit according to the present invention is described based on an embodiment described below. In this embodiment, the ultraviolet ray blocking unit 20 according to the embodiment is described with reference to FIG. 2 to FIG. 4B used in the description of the ultraviolet ray irradiation device 10A according to the embodiment 1 described previously.

Figure 2:
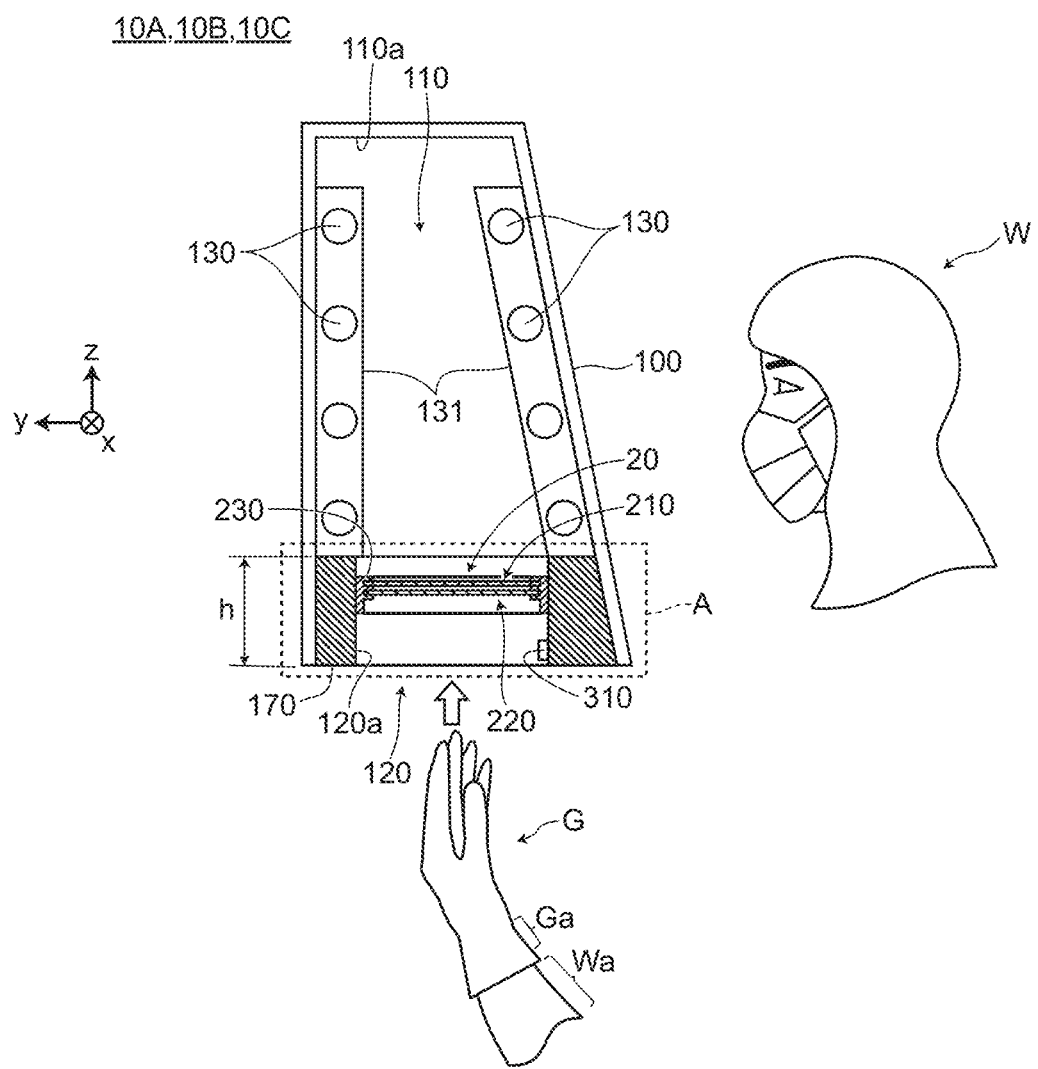
FIG. 2 is a longitudinal cross-sectional view of a side surface of the ultraviolet ray irradiation device shown in FIG. 1 as viewed in a direction indicated by an arrow x.

As shown in FIG. 2, FIG. 4A and FIG. 4B, the ultraviolet ray blocking unit 20 according to the embodiment includes:

the first ultraviolet ray blocking elastic body 210; the second ultraviolet ray blocking elastic body 220; and the frame body 230. The ultraviolet ray blocking unit 20 having such a configuration can be detachably mounted (mountable and removable) on the sterilization chamber housing 100.

In the ultraviolet ray irradiation device 10A according to the embodiment 1 the sterilization chamber 100 includes the sterilization chamber housing member 170 (see FIG. 2, FIG. 5 and FIG. 6). Accordingly, the frame body 230 is detachably mounted on the sterilization chamber housing member 170. In this manner, by detachably mounting the frame body 230 which forms one of constitutional elements of the ultraviolet ray blocking unit 20 on the sterilization chamber housing member 170, the ultraviolet ray blocking unit 20 can be detachably mounted on the sterilization chamber housing member 170. Detachable mounting of the ultraviolet ray blocking unit 20 according to the embodiment on the sterilization chamber housing member 170 means that the ultraviolet ray blocking unit 20 is detachably mountable on the sterilization chamber housing 100.

In mounting the ultraviolet ray blocking unit 20 on the sterilization chamber housing member 170, the frame body 230 on which the first ultraviolet ray blocking elastic body 210 and the second ultraviolet ray blocking elastic body 220 are mounted is inserted into the sterilization chamber housing 100 from below the sterilization chamber housing 100, and the frame body 230 is fixed by a fixing means such as a screw (not shown in the drawings). In removing the ultraviolet ray blocking unit 20 from the sterilization chamber housing member 170, the fixing means such as a screw which fixes the frame body 230 is removed, and the ultraviolet ray blocking unit 20 is drawn out downwardly. With such an operation, the ultraviolet ray blocking unit can be easily mounted on or removed from the sterilization chamber housing 100.

In this embodiment, the case is exemplified where the ultraviolet ray blocking unit 20 includes: the first ultraviolet ray blocking elastic body 210; the second ultraviolet ray blocking elastic body 220; and the frame body 230. However, the sterilization chamber housing member 170 may be included in the ultraviolet ray blocking unit 20. In this case, the sterilization chamber housing member 170 may be detachably mounted on the sterilization chamber housing 100. Also in this case, a bare skin detection unit 310 which forms an insertion depth detection unit is disposed in the sterilization chamber housing member 170. Accordingly, when the sterilization chamber housing member 170 is removed from the sterilization chamber housing 100, the bare skin detection unit 310 is also removed. However, by detachably mounting the bare skin detection unit 310 on the sterilization chamber housing member 170, in exchanging the ultraviolet ray blocking unit 20, the bare skin detection unit 310 can be mounted on the sterilization chamber housing member 170 of the new ultraviolet ray blocking unit 20.

In this manner, the ultraviolet ray blocking unit 20 is configured to be detachably mounted on the sterilization chamber housing 100. Accordingly, when the ultraviolet ray blocking elastic bodies 210, 220 are deteriorated or broken, the ultraviolet ray blocking unit 20 can be exchanged as a whole together with the ultraviolet ray blocking elastic bodies 210, 220. As a result, maintenance of the ultraviolet ray irradiation device 10A can be performed easily.

In this embodiment, the ultraviolet ray blocking unit 20 has been described with reference to FIG. 2, FIG. 4A and FIG. 4B used in the description of the previously mentioned ultraviolet ray irradiation device 10A according to the embodiment 1. However, also in the ultraviolet ray irradiation device 10B according to the embodiment 2 and the ultraviolet ray irradiation device 10B according to the modification of the embodiment 2, the ultraviolet ray blocking unit 20 can be formed of the first ultraviolet ray blocking elastic body 250, 270, the second ultraviolet ray blocking elastic body 260, 280, and the frame body 230. Also in the ultraviolet ray irradiation device 10C according to the embodiment 3, the ultraviolet ray blocking unit 20 can be formed of the first ultraviolet ray blocking elastic body 210, the second ultraviolet ray blocking elastic body 220, and the frame body 230. Further, with respect to the ultraviolet ray irradiation device 10B according to the embodiment 2, the ultraviolet ray irradiation device 10B according to the modification of the embodiment 2, and the ultraviolet ray irradiation device 10C according to the embodiment 3, the respective ultraviolet ray blocking units 20 may be formed of the ultraviolet ray blocking unit 20 which includes the sterilization chamber housing member 170.

The above-mentioned ultraviolet ray blocking unit 20 is inserted into and fixed to the inside of the sterilization chamber housing 100. However, the present invention is not limited to such a configuration. For example, the ultraviolet ray blocking unit 20 may be mounted on a lower end of the sterilization chamber housing 100.

The present invention is not limited to the above-mentioned embodiments, and various modifications can be carried out without departing from the gist of the present invention. For example, the following modifications can be carried out.

(1) Space portions (for example, the space portions 211*b*, 221*b* in the embodiment 1) may be formed at terminal end portions of the cuts C of the respective ultraviolet ray blocking elastic bodies (for example, end portions of the respective ultraviolet ray blocking elastic bodies in the above-mentioned respective embodiments on a peripheral edge portion side) thus forming a neck portion of a certain size on end portions of the elastic members each formed between the respective cuts C on a root side (the end portions on a side opposite to the distal end portions which form the free ends). This configuration may be described hereinafter by taking the first ultraviolet ray blocking elastic body 210 as an example.

Figure 13:
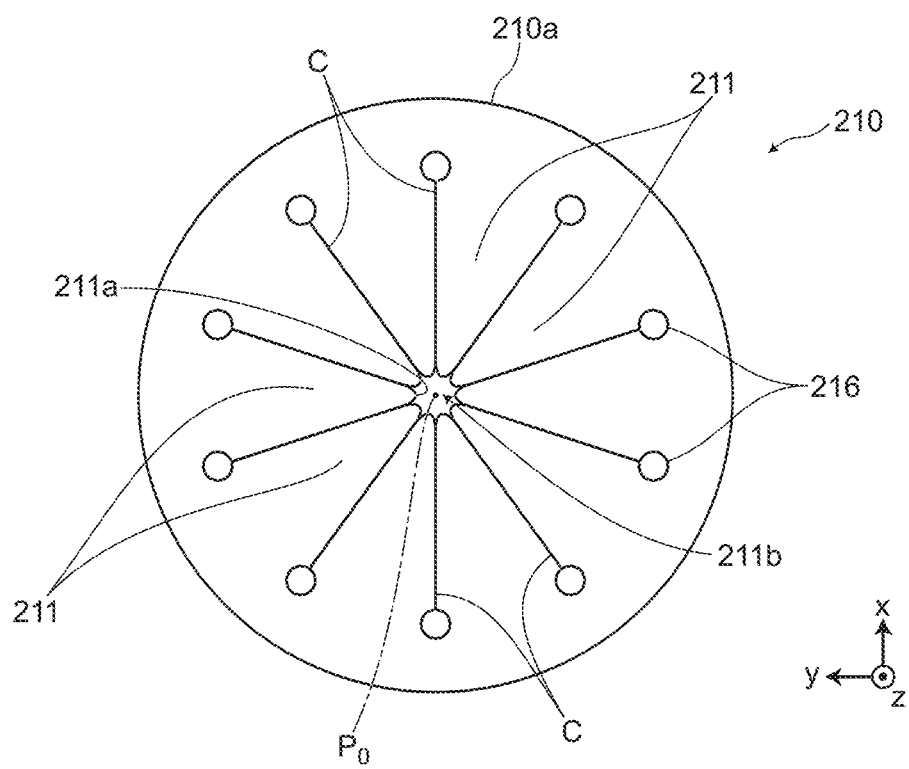
FIG. 13 is a view where a necked portion of a certain size is formed on end portions on a root side (end portions on a side opposite to distal end portions 211a which form free ends) of respective elastic members 221 formed between respective cuts C.

FIG. 13 is a view showing an example where a necked portion of a certain size is formed on end portions of the respective elastic members 211 each formed between the cuts C on a root side (the end portions on a side opposite to the respective distal end portions 211*a* which form the free ends). In the example shown in FIG. 13, a circular space portion 216 is formed on terminal portions of the cuts C of the ultraviolet ray blocking elastic body 210 (an end portion of the ultraviolet ray blocking elastic body 210 on a peripheral edge portion 210*a* side). With such a configuration, a neck portion of a certain size is formed on the end portion on a root side of each elastic member 211 formed between the respective cuts C (the end portion on a side opposite to the distal end portion 211*a* which forms the free end). The shape of the space portion 216 is not limited to a circular shape, and the space portion 216 may be formed in various shapes such as an elliptical shape or a quadrangular shape. It is preferable that the shape and the size of the space portion be a shape or a size which make it difficult for the space portions to overlap with each other when the respective ultraviolet ray blocking elastic bodies are stacked.

As shown in FIG. 13, by forming the neck portion of a certain size at the end portion of each elastic member 211 formed between the respective cuts C on a root side (the end portion on a side opposite to the distal end portion 211a which forms a free end), each elastic member 211 becomes easily bendable. Accordingly, when an operator W inserts into a hand on which the glove G is mounted into the sterilization chamber housing 100 by penetrating the ultraviolet ray blocking elastic body, the penetration of the hand on which the glove G is mounted can be easily performed, and the removal of the penetrated hand (the hand on which the glove G is mounted) by drawing can be also easily performed.

In FIG. 13, the description has been made by taking the first ultraviolet ray blocking elastic body 210 as an example. However, the above-mentioned operation can be performed substantially in the same manner also with respect to the second ultraviolet ray blocking elastic body 220. The above-mentioned operation can be performed also with respect to the first ultraviolet ray blocking elastic bodies 250, 270 and the second ultraviolet ray blocking elastic bodies 260, 280 used in the embodiment 2 and the modification of the embodiment 2.

(2) In the above-mentioned respective embodiments, the plurality of cuts C formed in each ultraviolet ray blocking elastic body are formed of a straight-line cut. However, the cuts C are not limited to a straight line, and may be formed of a curved line. Further, in the above-mentioned respective embodiments, the number of cuts is 10. However, the number of cuts is not limited to 10. Further, an angle made between the cuts disposed adjacently to each other is not limited to a fixed value. Modifications of the cuts C are described hereinafter.

Figure 14A:
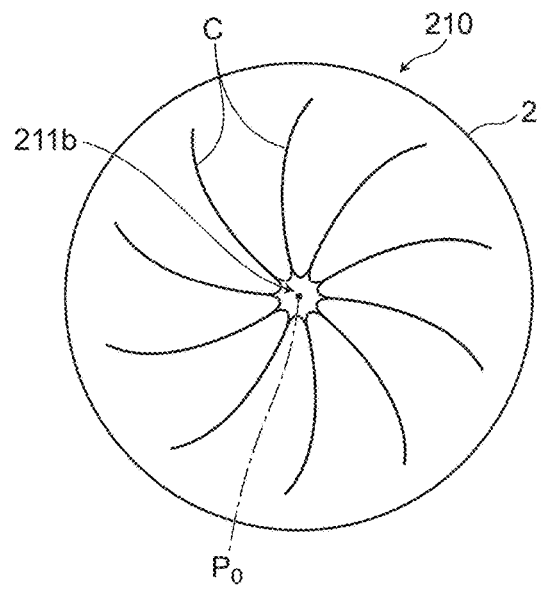
FIG. 14A to FIG. 14D are views for describing modifications of the cuts C.
Figure 14B:
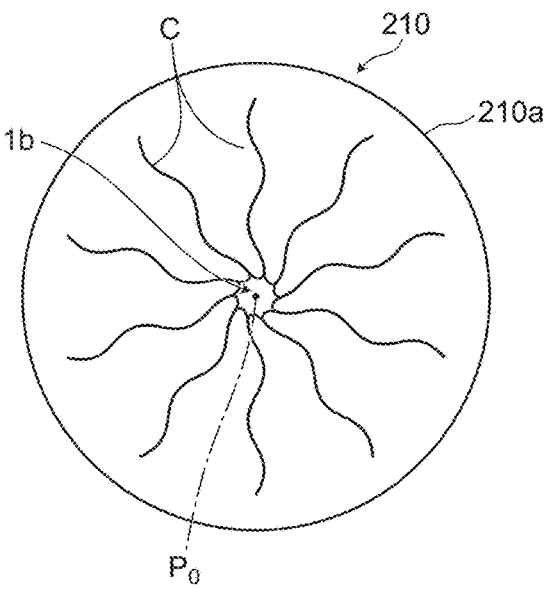
Figure 14C:
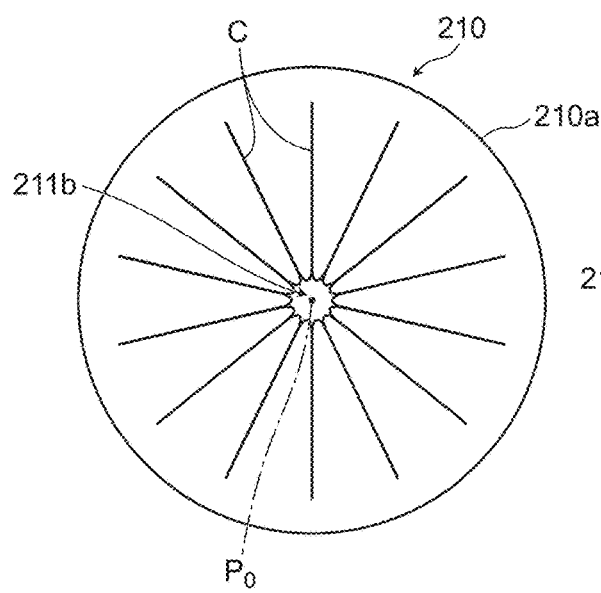
Figure 14D:
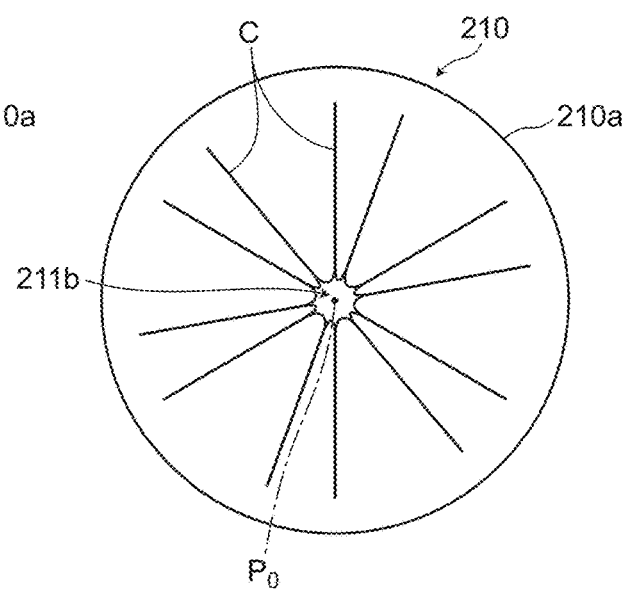

FIG. 14A to FIG. 14D are views for describing modifications of the cut C. FIG. 14A and FIG. 14B are views showing one example where the cut C is formed of a curved line. FIG. 14C is a view showing a case where the number of cuts C is other than 10 (for example, 14). FIG. 14D exemplifies a case where an angle made between the cuts C disposed adjacently to each other is not fixed. In FIG. 14A to FIG. 14D, the cuts C of the first ultraviolet ray blocking elastic body 210 are exemplified. However, the cuts C may be formed in the second ultraviolet ray blocking elastic body 220 substantially in the same manner. The cuts C may be formed substantially in the same manner in the first ultraviolet ray blocking elastic bodies 250, 270 and the second ultraviolet ray blocking elastic bodies 260, 280 used in the embodiment 2 and the modification of the embodiment 2.

In FIG. 14A and FIG. 14B, the cuts C are formed of a curved line. Also in a case where the cuts C are formed of a curved line, such cuts are included in "a plurality of cuts formed along lines extending radially from a predetermined position of the ultraviolet ray blocking elastic body to a peripheral edge portion of the ultraviolet ray blocking elastic body".

Even when the cuts C formed in each ultraviolet ray blocking elastic body are the cuts C shown in FIG. 14A to FIG. 14D, the ultraviolet ray irradiation devices described in the above-mentioned embodiments can be configured. The ultraviolet ray blocking elastic bodies having the cuts C shown in FIG. 14A to FIG. 14D may be used in suitable combination.

(3) In the above-mentioned respective embodiments, the case is exemplified where the space portion surrounded by the respective distal end portions of the respective elastic members of each ultraviolet ray blocking elastic body is formed at the position where such distal end portions marge. However, the space portion may not be formed.

For example, to describe the first ultraviolet ray blocking elastic body 210, at the position where the respective distal end portions 211a of the respective elastic members 211 of the first ultraviolet ray blocking elastic body 210 marge, the space portion 211b surrounded by the respective distal end portions 211a is formed. However, the space portion 211b may not be formed. That is, the position where the distal end portions 211a of the respective elastic members 211 marge may be the center Po of the ultraviolet ray blocking elastic body 210. Such a configuration may be adopted substantially in the same manner also by the second ultraviolet ray blocking elastic body 220. Further, such a configuration may be also adopted substantially in the same manner by the first ultraviolet ray blocking elastic bodies 250, 270 and the second ultraviolet ray blocking elastic bodies 260, 280 used in the embodiment 2 and the modification of the embodiment 2.

(4) In the above-mentioned respective embodiments, the case is exemplified where place surfaces of the ultraviolet ray blocking elastic bodies 210, 220, 250, 260, 270, 280 are formed of a flat smooth surface. However, unevenness may exist on the plate surfaces. Particularly, in the case where two ultraviolet ray blocking elastic bodies are stacked in a contact state, because of the existence of the unevenness on the plate surfaces of the respective ultraviolet ray blocking elastic bodies (mainly the plate surfaces of the respective elastic members), it is possible to prevent the occurrence of the drawback that two ultraviolet ray blocking elastic bodies are brought into close contact with each other so that it is difficult to separate these ultraviolet ray blocking elastic bodies from each other.

That is, when the plate surfaces of two sheets of ultraviolet ray blocking elastic bodies (for example, first ultraviolet ray blocking elastic body 210 and the second ultraviolet ray blocking elastic body 220) are formed of a flat smooth surface, depending on a material of the ultraviolet ray blocking elastic body, when the first ultraviolet ray blocking elastic body 210 and the second ultraviolet ray blocking elastic body 220 are stacked in a contact state, there may be a case where the first ultraviolet ray blocking elastic body 210 and the second ultraviolet ray blocking elastic body 220 are brought into close contact to each other so that it is difficult to separate these ultraviolet ray blocking elastic bodies from each other.

When the first ultraviolet ray blocking elastic body 210 and the second ultraviolet ray blocking elastic body 220 are brought into close contact with each other so that it is difficult to separate the ultraviolet ray blocking elastic bodies from each other, there may be a case where a drawback arises that a penetration operation at a time of penetrating the hand on which the glove G is mounted and a drawing operation at the time of drawing the penetrated hand (the hand on which the glove G is mounted) cannot be performed smoothly. On the other hand, when unevenness exist on the plate surface of at least one of the ultraviolet ray blocking elastic bodies, the occurrence of such a drawback can be prevented. Although unevenness which exist on the plate surface is not particularly limited, a plurality of fine projections or wave-shaped unevenness and the like can be exemplified.

(5) In the above-mentioned respective embodiments, the case is exemplified where two sheets of ultraviolet ray blocking elastic bodies formed of the first ultraviolet ray blocking elastic body (for example, first ultraviolet ray blocking elastic body 210) and the second ultraviolet ray blocking elastic body (for example, second ultraviolet ray blocking elastic body 220) are used for forming the ultraviolet ray blocking elastic body. However, the number of sheets of the ultraviolet ray blocking elastic bodies is not limited to 2, and may be 3 or more.

In the case where the number of sheets of the ultraviolet ray blocking elastic bodies is set to 3 or more, in a state where 3 or more ultraviolet ray blocking elastic bodies are stacked, the ultraviolet ray blocking elastic bodies are mounted in a frame body such that the cuts of at least one sheet of ultraviolet ray blocking elastic body among 3 or more sheets of respective ultraviolet ray blocking elastic bodies is "displaced" along the plate surfaces of the respective ultraviolet ray blocking elastic bodies with respect to the plurality of cuts of other ultraviolet ray blocking elastic bodies.

In this manner, in the ultraviolet ray irradiation device according to the present invention, with respect to the respective ultraviolet ray blocking elastic bodies mounted on the frame body, the respective ultraviolet ray blocking elastic bodies are mounted on the frame body such that the plurality of cuts formed in at least one sheet of ultraviolet ray blocking elastic body among the respective ultraviolet ray blocking elastic bodies are "displaced" along the plate surfaces of the respective ultraviolet ray blocking elastic bodies with respect to the plurality of cuts of other ultraviolet ray blocking elastic bodies. With respect to 3 or more sheets of respective ultraviolet ray blocking elastic bodies, it is more preferable that the respective ultraviolet ray blocking elastic bodies be mounted on the frame body such that the cuts of all ultraviolet ray blocking elastic bodies are "displaced" from each other along the plate surfaces of the respective ultraviolet ray blocking elastic bodies.

(6) In the above-mentioned embodiments, the insertion depth detection unit which detects that the hand on which the glove G is mounted is inserted into the sterilization chamber 110 by a predetermined depth is formed as the bare skin detection unit 310. However, the insertion depth detection unit is not limited to the bare skin detection unit 310. For example, in a case where identifiers for identifying individual operators are attached to gloves which the individual operators use, an operator identifier detection unit which detects the operator identifiers can be also used as the insertion depth detection unit. Besides these units, various modifications can be carried out with respect to the insertion depth detection unit. The following (a) to (d) show such modifications of the insertion depth detection unit.

(a) In the first modification of the insertion depth detection unit, an insertion restricting unit (not shown in the drawings) which restricts an insertion depth of a hand on which a glove G is mounted is disposed in the sterilization chamber 110, and a touch sensor is mounted on the insertion restricting unit. Then, the touch sensor detects that a predetermined portion (for example, a fingertip of any one of five fingers or a valley portion formed between two fingers disposed adjacently to each other) of the hand on which the glove G is mounted touches the insertion restricting unit, and outputs an insertion depth detection signal.

(b) In a second modification of the insertion depth detection unit, a camera (not shown in the drawings) is disposed in the sterilization chamber 110, and a hand on which a glove G is mounted is photographed when the hand on which the glove G is mounted is inserted into the sterilization chamber 110. Then, the insertion depth detection unit detects that the hand on which the glove G is mounted is inserted into the sterilization chamber 110 by a predetermined depth based on a photographed image photographed by the camera, and outputs an insertion depth detection signal.

(c) In a third modification of the insertion depth detection unit, a light emitting element and a light receiving element (not shown in the drawings) are arranged to face each other at a predetermined position in the sterilization chamber 110. Then, the insertion depth detection unit detects that a predetermined portion (for example, a fingertip of any one of five fingers) of a hand on which a glove G is mounted blocks a light from the light emitting element based on a signal transmitted from the light receiving element, and outputs an insertion depth detection signal which indicates that the hand on which the glove G is mounted is inserted into the sterilization chamber 110 by a predetermined depth.

(d) It is possible to selectively combine the bare skin detection unit 310 described in the embodiment 1, the above-mentioned operator identifier detection unit, the first modification of the insertion depth detection unit described in the above-mentioned (a), the second modification of the insertion depth detection unit described in the above-mentioned (b), and the third modification of the insertion depth detection unit described in the above-mentioned (c).

(7) In the above-mentioned respective embodiments, the description has been made by assuming that the glove G is a glove of a type having a short length which covers a range from the fingertips to the wrist of the operator W. However, the glove G is not limited to such a glove, and the glove G may be a glove of a type having a long length which can cover a range from the fingertips to a portion close to an elbow of an operator W. The glove G and an arm cover may be used in combination. When the glove G and the arm cover are used in combination, it is sufficient to use at least one of the above-mentioned operator identifier detection unit and the respective insertion depth detection units in (a) to (c) described in the above-mentioned (7).

Figure 15:
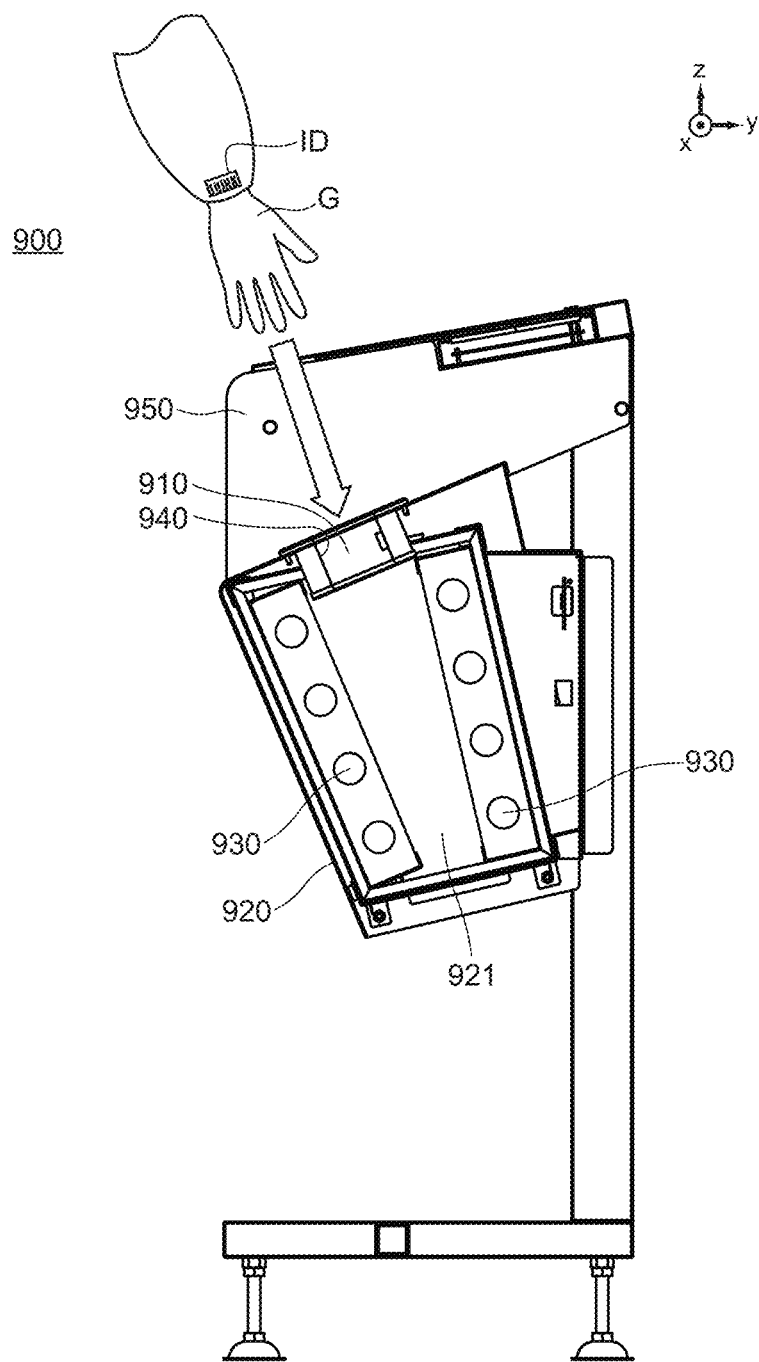
FIG. 15 is a perspective view for describing an ultraviolet ray irradiation device 900 described in JP 2017-63900 A.

(8) The respective ultraviolet ray irradiation devices 10A, 10B (including modifications), and 10C shown in the above-mentioned embodiments are formed of an ultraviolet ray irradiation device of a type where, in inserting a hand on which a glove G is mounted into the sterilization chamber 110, the hand on which the glove G is mounted is inserted in an upward direction from below. However, like the ultraviolet ray irradiation device described in the above-mentioned "Description of the Related Art" (see FIG. 15), an ultraviolet ray irradiation device of a type where a hand on which a glove G is mounted is inserted in a downward direction from above may be also adopted. Although not shown in the drawings, an ultraviolet ray irradiation device of a type where a hand on which a glove G is mounted is inserted in an oblique upward direction, in an oblique downward direction or in a horizontal direction may be also adopted.

What is claimed is:

1. An ultraviolet ray irradiation device which sterilizes a surface of a glove which is mounted on a hand of an operator and is made of an ultraviolet ray non-transmitting material by irradiating ultraviolet rays to the glove, the ultraviolet ray irradiation device comprising:

a sterilization chamber housing formed of an ultraviolet ray blocking member configured to block the ultraviolet rays, the sterilization chamber housing having a sterilization chamber therein, and having an insertion opening through which the hand on which the glove is mounted is insertable into the sterilization chamber;

an ultraviolet ray irradiation unit disposed in the sterilization chamber housing and configured to irradiate the ultraviolet rays to the sterilization chamber;

an ultraviolet ray blocking elastic body formed of a thin plate-like member having ultraviolet ray non-transmitting property and elasticity, disposed so as to traverse an insertion direction of the hand on which the glove G is mounted when the hand on which the glove G is mounted is inserted into the sterilization chamber through the insertion opening, and allowing the hand on which the glove G is mounted to penetrate the ultraviolet ray blocking elastic bodies; and a frame body disposed along a peripheral edge portion of the insertion opening, the frame body allowing the respective ultraviolet ray blocking elastic bodies to be mounted on the frame body by supporting peripheral edge portions of the respective ultraviolet ray blocking elastic bodies in a state where a plurality of the ultraviolet ray blocking elastic bodies are stacked, wherein the ultraviolet ray blocking elastic body is formed such that a plurality of cuts are formed in the ultraviolet ray blocking elastic body along a plurality of lines extending radially from a predetermined position on a plate surface of the ultraviolet ray blocking elastic body toward a peripheral edge portion of the ultraviolet ray blocking elastic body thus forming the plurality of elastic members between the cuts, wherein a distal end portion of each of the plurality of elastic members which is positioned on a side of the predetermined position forms a free end which is freely movable in a frontward and backward direction of the ultraviolet ray blocking elastic body, and the respective ultraviolet ray blocking elastic bodies mounted on the frame body are mounted on the frame body such that the plurality of cuts formed in at least one ultraviolet ray blocking elastic body among the respective ultraviolet ray blocking elastic bodies are displaced with respect to the plurality of cuts of other ultraviolet ray blocking elastic bodies along the plate surfaces.

2. The ultraviolet ray irradiation device according to claim 1, wherein the respective ultraviolet ray blocking elastic bodies mounted on the frame body are formed of an ultraviolet ray blocking elastic body having the same number of cuts.

3. The ultraviolet ray irradiation device according to claim 1, wherein among the respective ultraviolet ray blocking elastic bodies mounted on the frame body, the ultraviolet ray blocking elastic body in which the cuts, the number of which differs from the number of cuts in other ultraviolet ray blocking elastic bodies, exist.

4. The ultraviolet ray irradiation device according to claim 1, wherein the respective ultraviolet ray blocking elastic bodies mounted on the frame body are formed of an ultraviolet ray blocking elastic body where a position at which respective distal end portions of the plurality of elastic members formed on the respective ultraviolet ray blocking elastic bodies merge exists at the same position in the respective ultraviolet ray blocking elastic bodies.

5. The ultraviolet ray irradiation device according to claim 1, wherein in the respective ultraviolet ray blocking elastic bodies mounted on the frame body, positions at which respective distal end portions of the plurality of elastic members formed on the respective ultraviolet ray blocking elastic bodies merge exist at positions spaced apart from each other in a diameter direction with respect to the respective ultraviolet ray blocking elastic bodies.

6. The ultraviolet ray irradiation device according to claim 1, wherein among the respective ultraviolet ray blocking elastic bodies mounted on the frame body, an unevenness exists on a plate surface of at least one ultraviolet ray blocking elastic body out of the ultraviolet ray blocking elastic bodies which face each other.

7. The ultraviolet ray irradiation device according to claim 1, wherein the respective ultraviolet ray blocking elastic bodies mounted on the frame body are stacked in a state where the respective ultraviolet ray blocking elastic bodies are disposed close to each other or in a state where the respective ultraviolet ray blocking elastic bodies are brought into contact with each other.

8. The ultraviolet ray irradiation device according to claim 1, wherein the respective ultraviolet ray blocking elastic bodies mounted on the frame body are stacked in a state where the respective ultraviolet ray blocking elastic bodies are spaced apart from each other with a predetermined distance therebetween.

9. The ultraviolet ray irradiation device according to claim 1, wherein at positions of the distal end portion of the plurality of elastic members, a space portion surrounded by the distal end portions is formed.

10. The ultraviolet ray irradiation device according to claim 1, wherein the frame body has antibacterial property.

11. An ultraviolet ray blocking unit which is detachably mounted on a sterilization chamber housing of an ultraviolet ray irradiation device which sterilizes a surface of a glove which is mounted on a hand of an operator and is made of an ultraviolet ray non-transmitting material by irradiating ultraviolet rays to the glove, the ultraviolet ray blocking unit preventing irradiation of the ultraviolet rays to the outside of the ultraviolet ray irradiation device when the operator inserts the glove into the ultraviolet ray irradiation device, wherein the ultraviolet ray irradiation device comprises:

a sterilization chamber housing formed of an ultraviolet ray blocking member configured to block the ultraviolet rays, the sterilization chamber housing having a sterilization chamber in the sterilization chamber housing, and having an insertion opening through which the hand on which the glove is mounted is insertable into the sterilization chamber;

an ultraviolet ray irradiation unit disposed in the sterilization chamber housing and configured to irradiate the ultraviolet rays to the sterilization chamber, the ultraviolet ray blocking unit comprises:

an ultraviolet ray blocking elastic body formed of a thin plate-like member having ultraviolet ray non-transmitting property and elasticity, disposed so as to traverse an insertion direction of the hand when the hand on which the glove G is mounted is inserted into the sterilization chamber through the insertion opening, and allowing the hand on which the glove G is mounted to penetrate the ultraviolet ray blocking elastic bodies; and a frame body disposed along a peripheral edge portion of the insertion opening, the frame body allowing the respective ultraviolet ray blocking elastic bodies to be mounted on the frame body by supporting peripheral edge portions of the respective ultraviolet ray blocking elastic bodies in a state where a plurality of the ultraviolet ray blocking elastic bodies are stacked, and the ultraviolet ray blocking elastic body is formed such that a plurality of cuts are formed in the ultraviolet ray blocking elastic body along a plurality of lines extending radially from a predetermined position on a plate surface of the ultraviolet ray blocking elastic body toward a peripheral edge portion of the ultraviolet ray blocking elastic body thus forming the plurality of elastic members between the cuts, wherein a distal end portion of each of the plurality of elastic members which is positioned on a side of the predetermined position forms a free end which is freely movable in a frontward and backward direction of the ultraviolet ray blocking elastic body, and the respective ultraviolet ray blocking elastic bodies mounted on the frame body are mounted on the frame body such that the plurality of cuts formed in at least one ultraviolet ray blocking elastic body among the respective ultraviolet ray blocking elastic bodies are displaced with respect to the plurality of cuts of other ultraviolet ray blocking elastic bodies along the plate surfaces.

* * * * *